(12) United States Patent
Cao et al.

(10) Patent No.: US 10,081,542 B2
(45) Date of Patent: Sep. 25, 2018

(54) NANOZYMES, METHODS OF MAKING NANOZYMES, AND METHODS OF USING NANOZYMES

(75) Inventors: Yunwei Charles Cao, Gainesville, FL (US); Chen Liu, Gainesville, FL (US); Hongyan Liu, Gainesville, FL (US); Zhongliang Wang, Gainesville, FL (US); Soon Hye Yang, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1146 days.

(21) Appl. No.: 13/641,590

(22) PCT Filed: Apr. 19, 2011

(86) PCT No.: PCT/US2011/032980
§ 371 (c)(1),
(2), (4) Date: Oct. 16, 2012

(87) PCT Pub. No.: WO2011/133504
PCT Pub. Date: Oct. 27, 2011

(65) Prior Publication Data
US 2013/0034532 A1 Feb. 7, 2013

Related U.S. Application Data

(60) Provisional application No. 61/325,922, filed on Apr. 20, 2010.

(51) Int. Cl.
*C12N 9/96* (2006.01)
*B82Y 5/00* (2011.01)
*A61K 47/48* (2006.01)
*A61K 38/00* (2006.01)

(52) U.S. Cl.
CPC .......... *B82Y 5/00* (2013.01); *A61K 47/48092* (2013.01); *A61K 47/48861* (2013.01); *A61K 47/48884* (2013.01); *C12N 9/96* (2013.01); *A61K 38/00* (2013.01)

(58) Field of Classification Search
None
See application file for complete search history.

(56) References Cited

U.S. PATENT DOCUMENTS

| 6,677,122 B2 | 1/2004 | Mirkin et al. |
| 7,550,441 B2 | 6/2009 | Farokhzad et al. |
| 2004/0052729 A1 | 3/2004 | Penades et al. |
| 2008/0279946 A1 | 11/2008 | Hainfeld |
| 2009/0053169 A1 | 2/2009 | Castillo et al. |

FOREIGN PATENT DOCUMENTS

| CA | 2648099 | 9/2008 |
| CA | 2648099 A1 | 9/2008 |
| EP | 1847600 A1 | 10/2007 |
| JP | 20010031308 | 11/2001 |
| JP | 2007289167 | 11/2007 |
| JP | 2008500364 | 1/2008 |
| JP | 2009534309 | 9/2009 |
| WO | 2002526383 | 8/2002 |
| WO | 2004045494 | 6/2004 |
| WO | WO2006044716 | 4/2006 |
| WO | WO 2008105773 A2 * | 9/2008 |
| WO | 2010009087 | 1/2010 |
| WO | 2010014895 A2 | 2/2010 |
| WO | 2010033913 A1 | 3/2010 |
| WO | 2010117957 | 10/2010 |

OTHER PUBLICATIONS

Suri et al., RNase: A Novel Enzyme for Treatment of Cancers, The Internet Journal of Oncology, vol. 5, pp. 1-8.*
Grunweller et al., Locked Nucleic Acid Oligonucleotides, Biodrugs, 2007, vol. 21, pp. 235-243.*
Li et al., Nanosize delivery as an emerging platform for cancer therapy, Cancer Biology and Therapy, 2008, vol. 7, pp. 1860-1862.*
Catalytic Behaviors of Enzymes Attached to Nanoparticles: The Effect of Particle Mobility Biotechnology and Bioengineering, Sep. 11, 2003, vol. 84, Issue 4, pp. 406-414.*
The International Preliminary Report on Patentability dated Nov. 1, 2012.
The International Search Report and Written Opinion dated Jan. 4, 2012.
Lee, et al., "Enhanced Bioaffinity Sensing Using Surface Plasmons, Surface Enzyme Reactions, Nanoparticles and Diffraction Gratings", Analyst 2008, 133, pp. 596-601.
Zhang, et al., "Recent Advances in Nanotechnology Applied to Biosensors", Sensors, 2009, vol. 9, pp. 1033-1053.
Kalaugher, Gold Nanoparticles and Bio-Bar Codes Bring Sensitive DNA Detection:, nanotechweb.org, May 6, 2004.
Catalytic Behaviors of Enzymes Attached to Nanoparticles: The Effect of Particle Mobility Biotechnology and Bioengineering, vol. 84, Issue 4, pp. 406-414, Jia et al., 2003.
Walter, et al., "A unified View of Ligand-Protected Gold Clusters as Superatom Complexes", PNAS, Jul. 8, 2008, vol. 105, No. 27, pp. 9157-9162.
Liu, Meiying, et al. "Highly sensitive protein detection using enzyme-labeled gold nanoparticle probes." Analyst 135.2 (2010): 327-331.
Youle, et al; RNase inhibition of human immunodeficiency virus infection of H9 cells; Proc. Natl. Acad. Sci. USA vol. 91, pp. 6012-6016, Jun. 1994, Medical Sciences; 6 pages.
Cover letter and Office Action for Japanese patent application 2013-506223, Applicant: University of Florida Research Foundation, Inc.; dated Jun. 16, 2015; 14 pages; Japanese Patent Office.
Xin Yu, et al., Carbon Nanotube Amplification Strategies for Highly Sensitive Immunodetection of Cancer Biomarkers, Journal of the American Chem Society, 128:34, Aug. 1, 2006, pp. 11199-11205.

(Continued)

Primary Examiner — Louise Wang Zhiying Humphrey
(74) Attorney, Agent, or Firm — Thomas | Horstemeyer, LLP

(57) ABSTRACT

Embodiments of the present disclosure provides for nanozymes, methods of making nanozymes, methods of using nanozymes, and the like.

17 Claims, 14 Drawing Sheets

Specification includes a Sequence Listing.

(56) References Cited

OTHER PUBLICATIONS

Londono, I. et al., Brief Review on Progresses in Enzyme-Gold Cytochemistry, Scanning Microscopy Supplement, Scanning Microscopy International, Chicago, IL, US, vol. 3, Jan. 1, 1989, pp. 7-14.
Rosi, Nathaniel L., et al., Oligonucleotide-modified gold nanoparticles for intracellular gene regulation, Science, American Association for the Adv of Science, US, 312:5776, May 19, 2006, pp. 1027-1030.
Ke, R. et al, Tandem conjunction of enzyme and antibody on silica nanoparticle for enzyme immunoassay, Analytical Biochemistry, Academic Press Inc, New York, 406:1, Nov. 1, 2010, pp. 8-13.
Reukov, Vladimir, et al., Proteins conjugated to poly(butyl cyanoacrylate) nanoparticles as potential neuroprotective agents, Biotechnology and Bioengineering, 108:2, Oct. 26, 2010, pp. 243-252.
Soon Hye Yang, Nanoparticle-based Cellular Machinery for the Degradation of Specific RNA and Protein, Aug. 1, 2011, pp. 1-58.
Supplemental Search Report for European Application EP 11 77 2525, based on PCT/US11/32980, dated Mar. 29, 2016.
English translation of JP 2007289167, Nov. 8, 2007.

\* cited by examiner

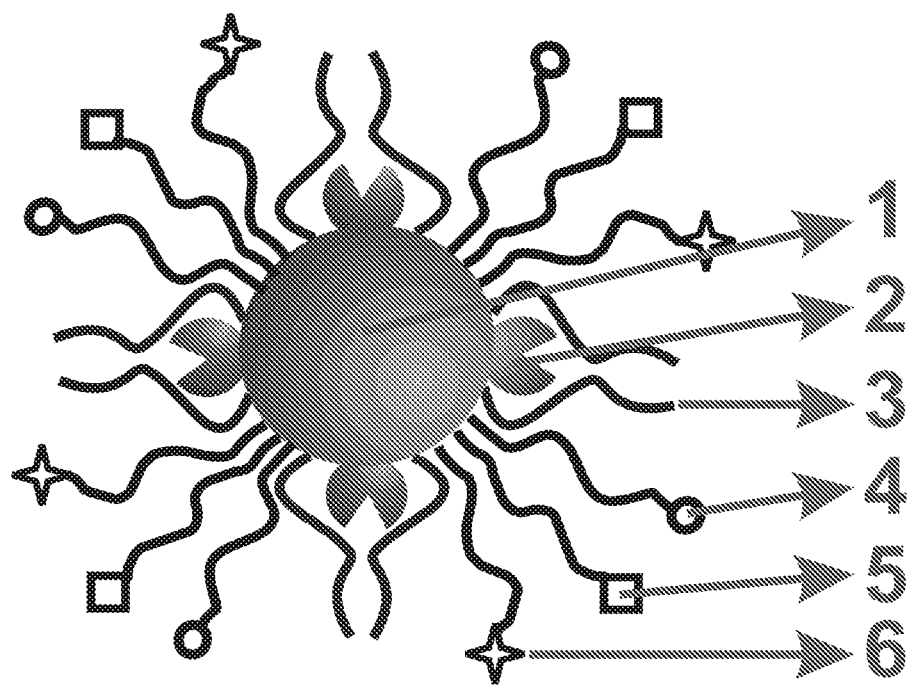
FIG. 1.1
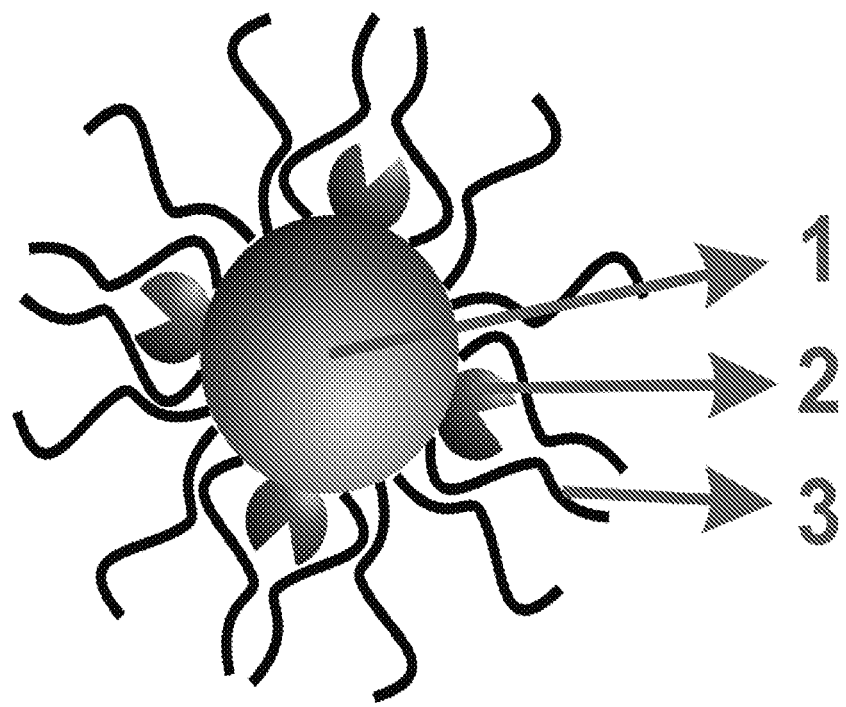
FIG. 1.2

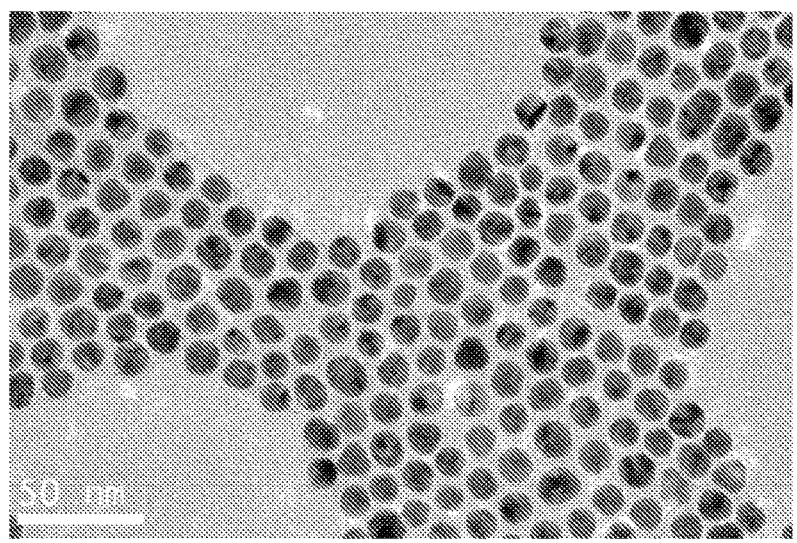
FIG. 1.3

HCV-specific nanoyme
1. -S--AAA AAA AAA-CCA GAG CAT CTG GCA CGT    SEQ ID No: 8
   5'-----GGA--GGU CUC GUA GAC CGT GCA--CCA-----3'
   HCV-mRNA    SEQ ID No: 9
2. Rnase A: 
HCV antisense oligonucleotide functionalized gold nanoparticles
3. -S--AAA AAA AAA-CCA GAG CAT CTG GCA CGT    SEQ ID No: 8
Control nanozyme
4. -S--AAA AAA AAA-AAA AAA AAA AAA AAA AAA
   SEQ ID No: 10
5.  ⟶ BSPP: bis(p-sulfonatophenyl)phenylphosphane
6. RNase-free water
FIG. 1.4

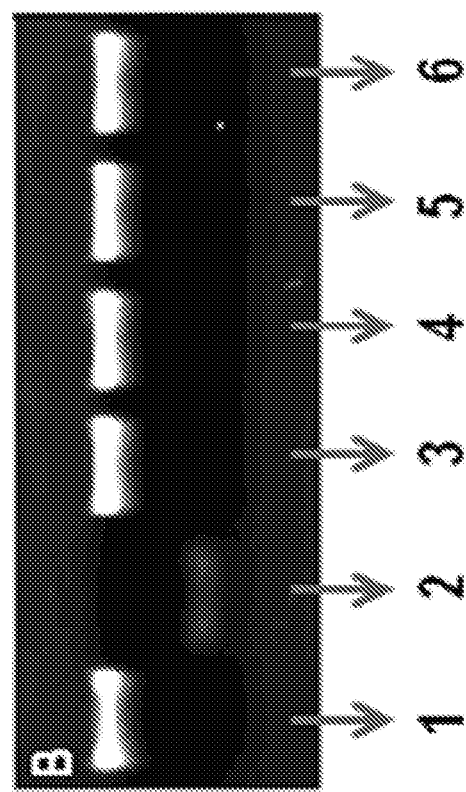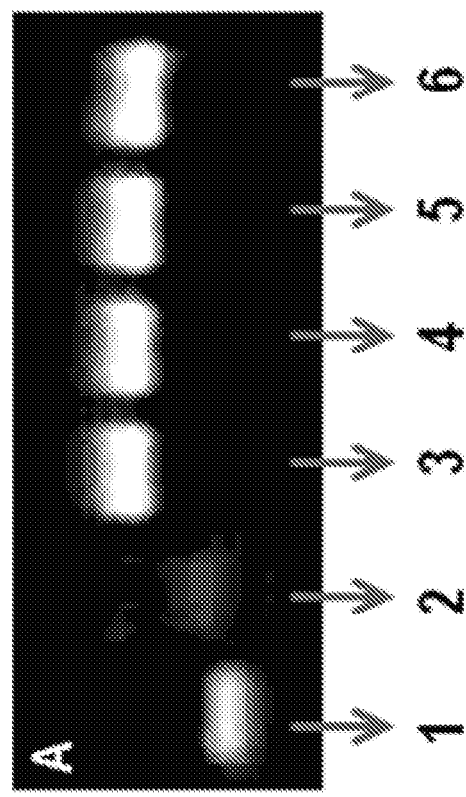
FIG. 1.5

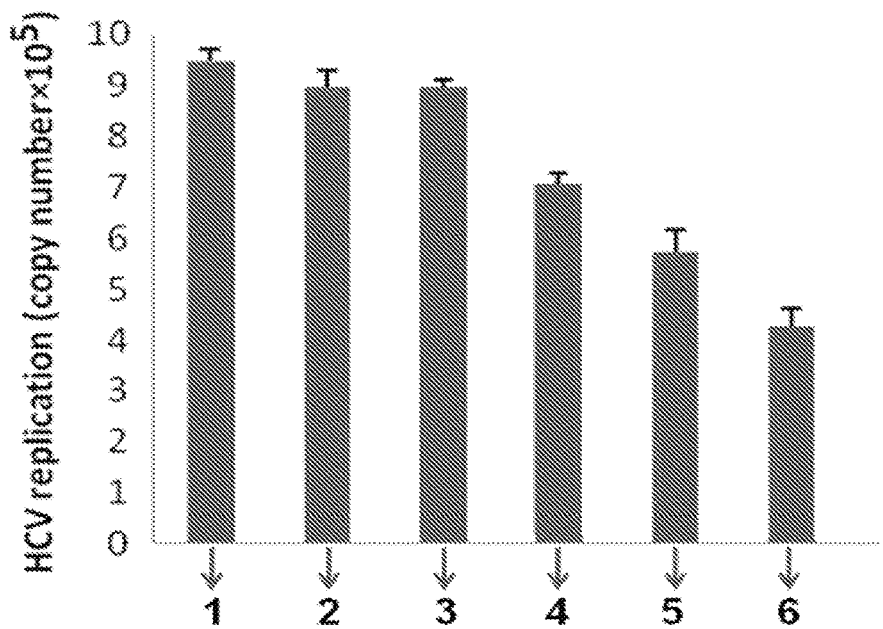
FIG. 1.6
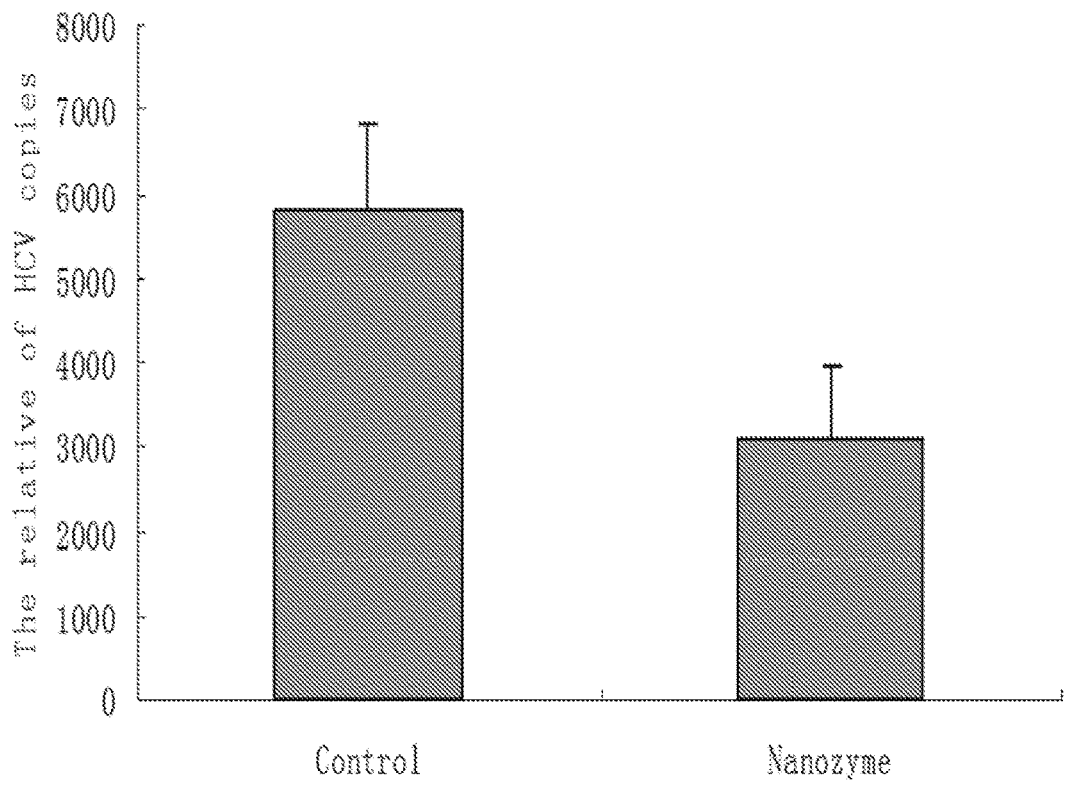
FIG. 1.7

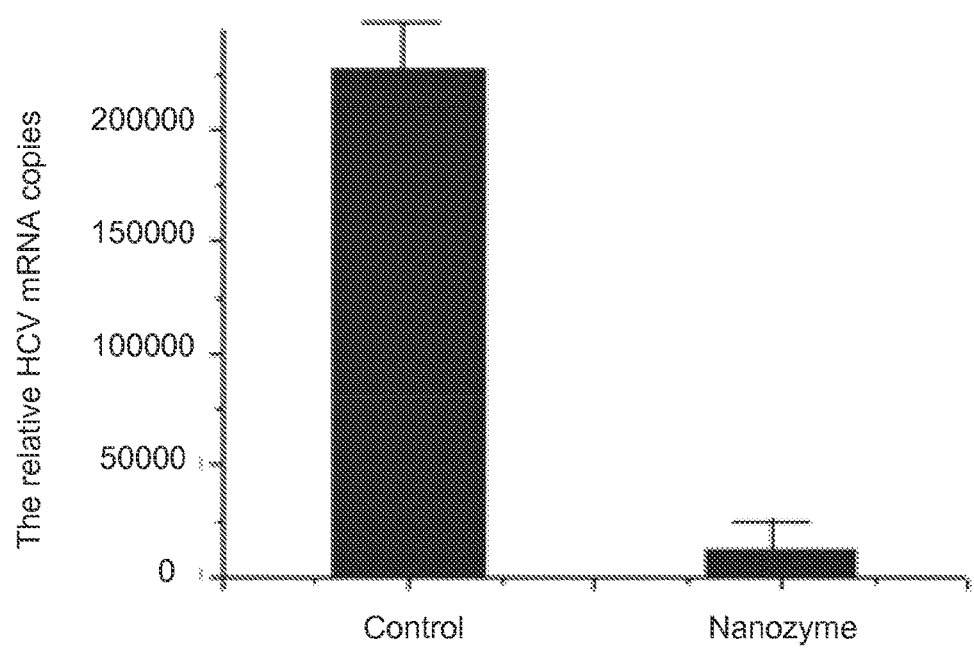
FIG. 1.8

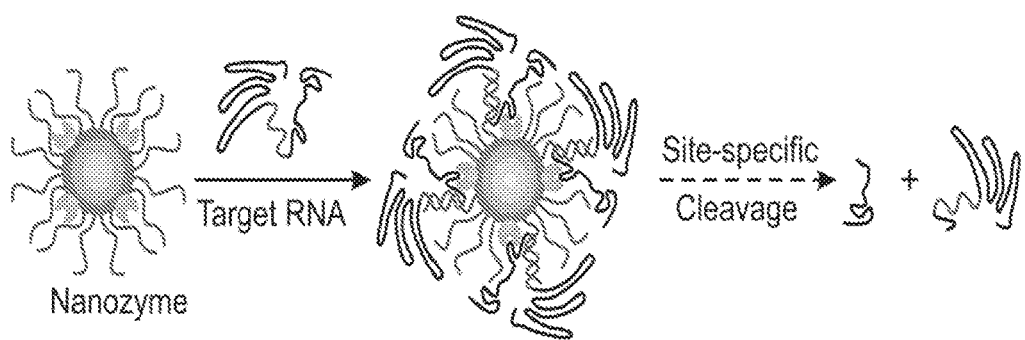
A.
```
                    322                         339
                     ↓         HCV RNA           ↓          SEQ ID No: 11
            5'-----GGA-GGU-CUC-GUA-GAC-CGU-GCA--CCA-----3'
B.  -S--AAA-AAA-AAA--CCA-GAG-CAT-CTG-GCA-CGT    SEQ ID No: 12
```
                                                SEQ ID No: 13
C. siRNA331:   GGU-CUC-GUA-GAC-CGU-GCA-C--TT (sense)
               TT--CCA-GAG-CAU-CUG-GCA-CGU-G   (antisense)
                                                SEQ ID No: 14
D.  -S--AAA-AAA-AAA--CCA-GAG-CAT-CTG-GCA-CGT    SEQ ID No: 15
FIG. 2.1

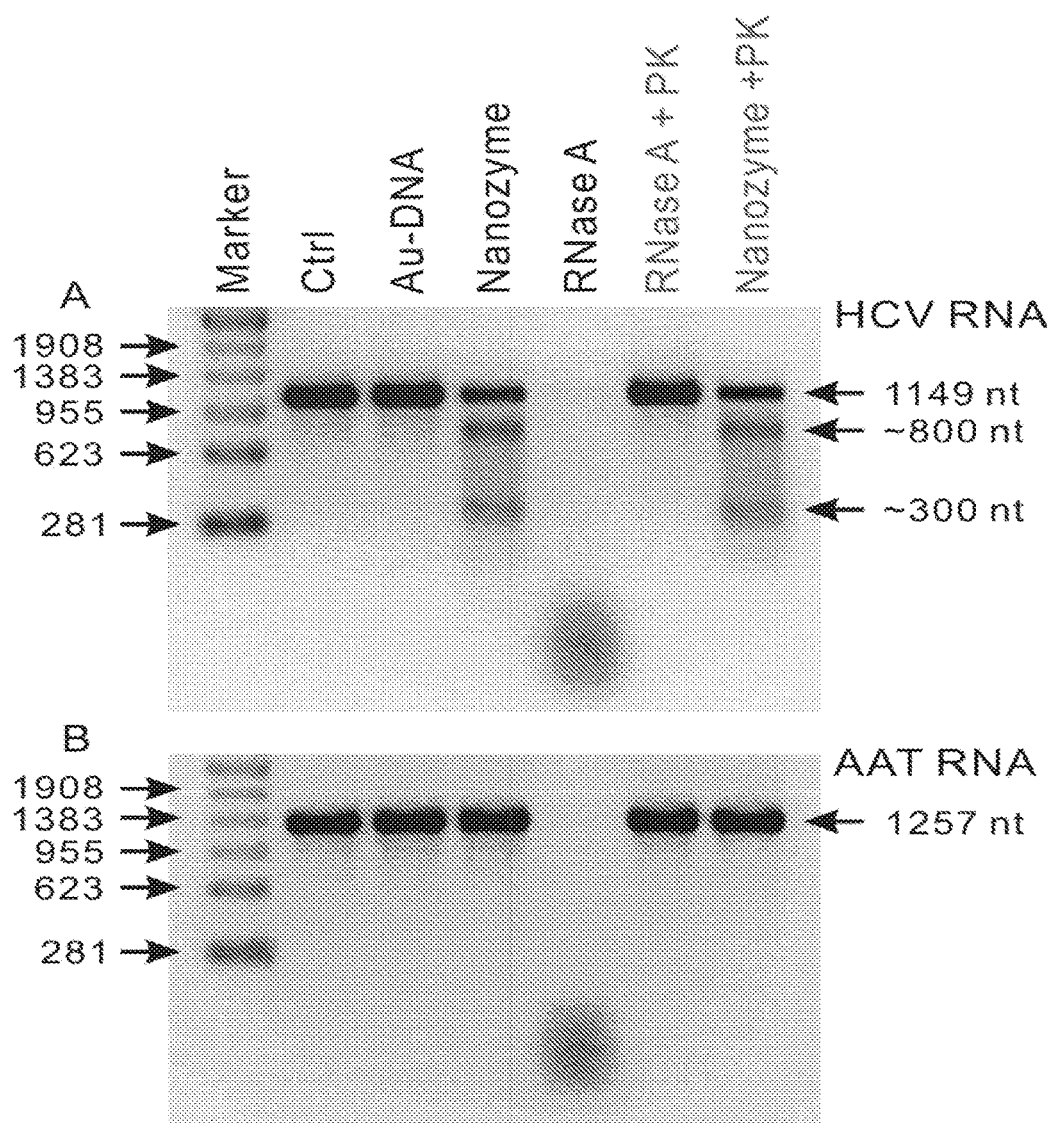
FIG. 2.2

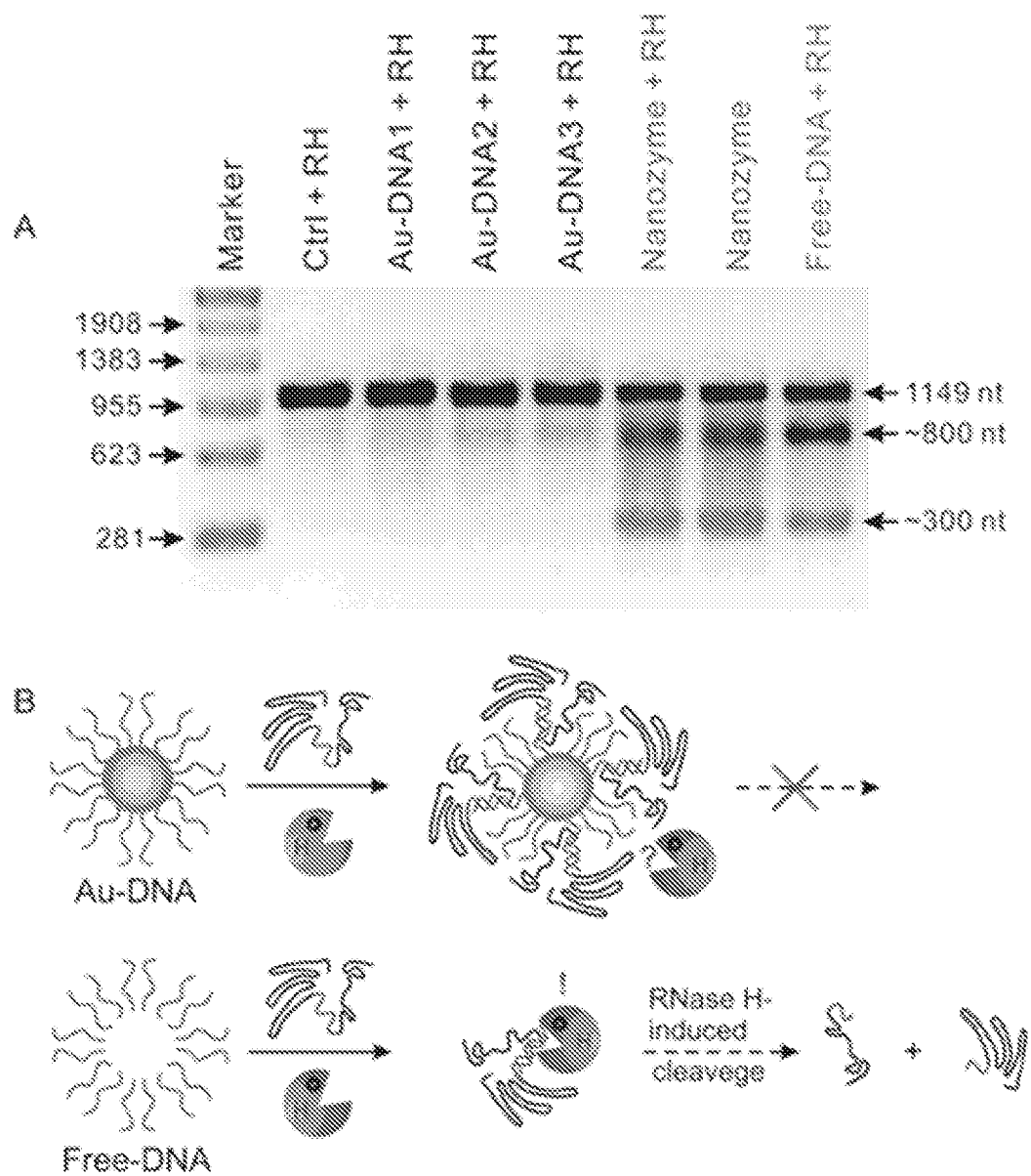
FIG. 2.3

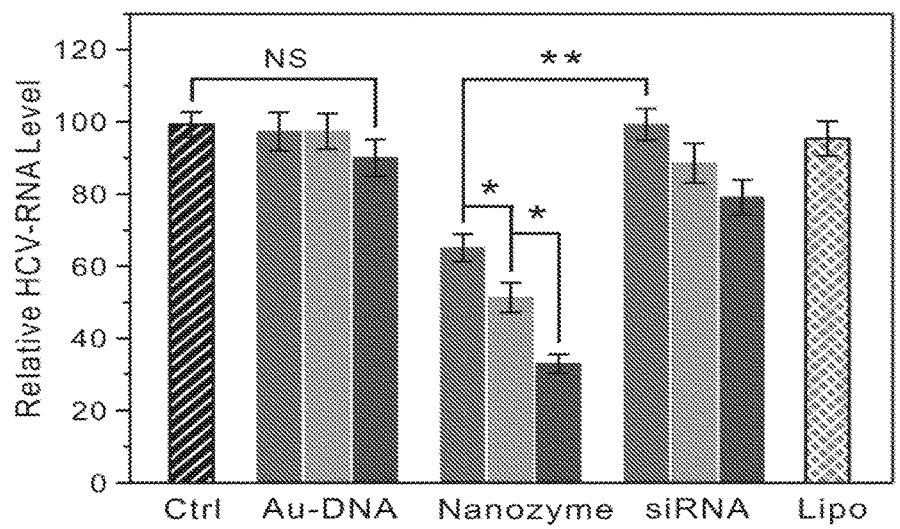
FIG. 2.4
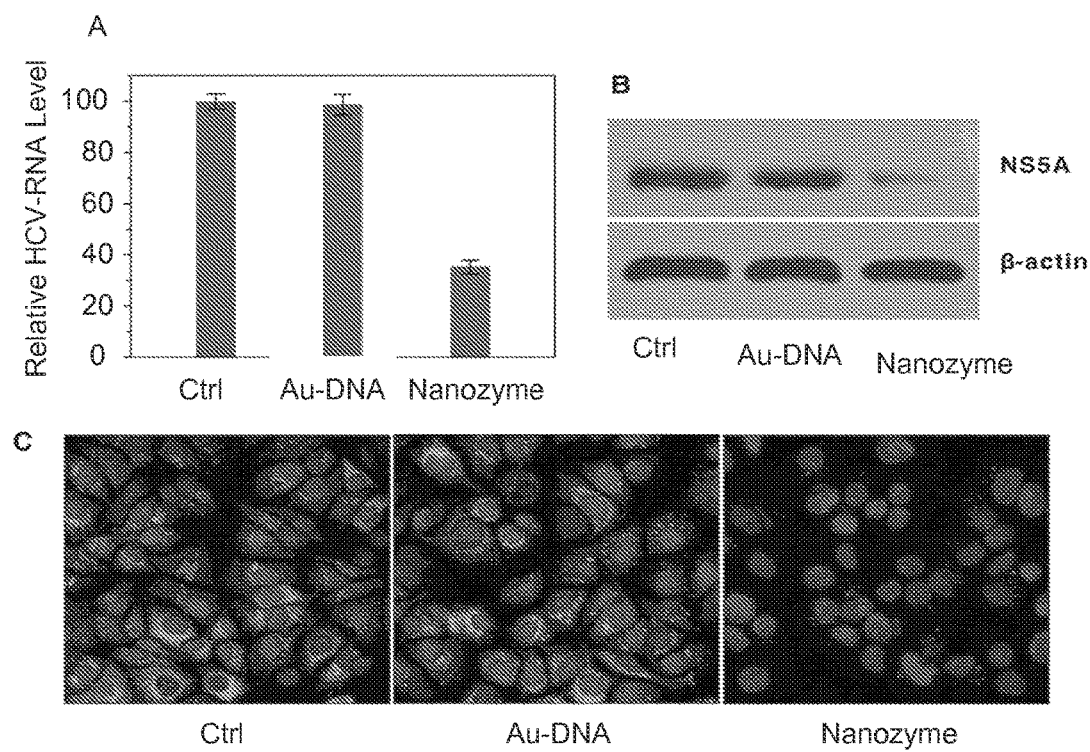
FIG. 2.5

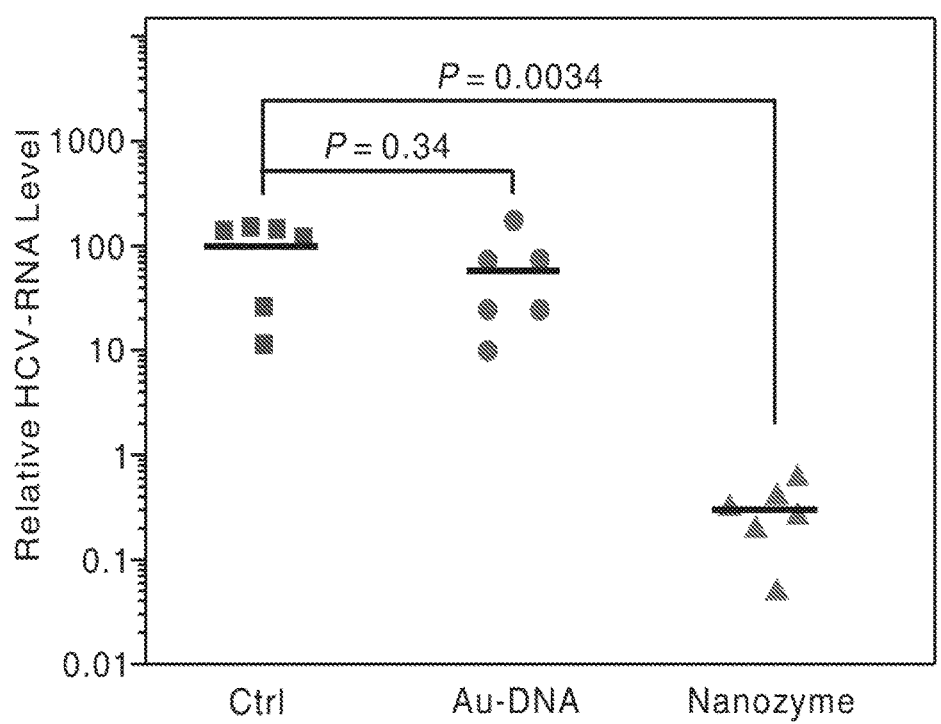
FIG. 2.6

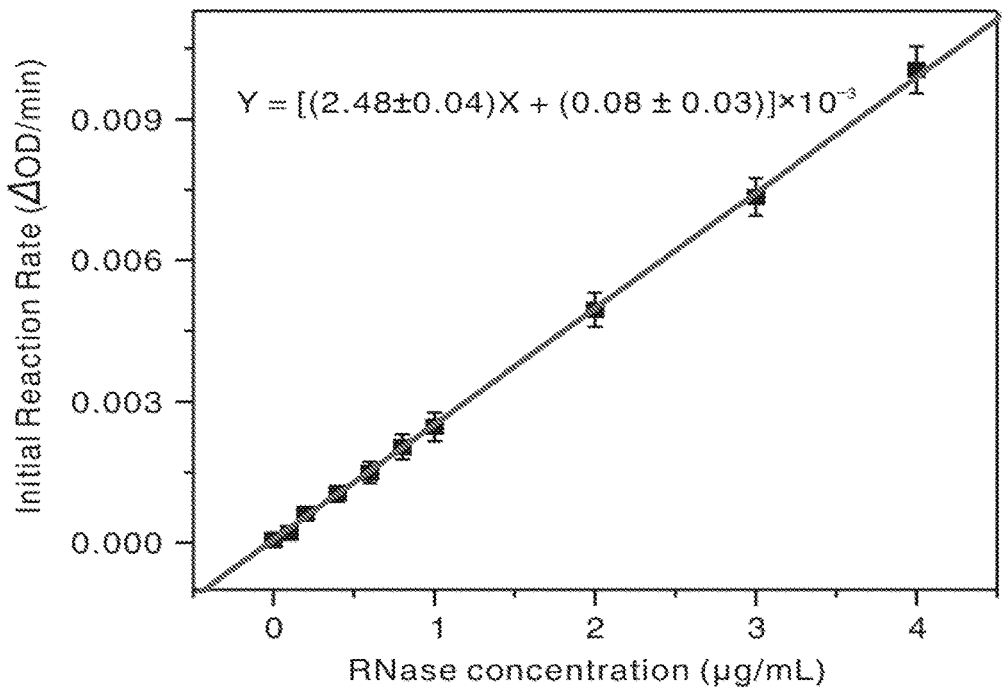
FIG. 2.7
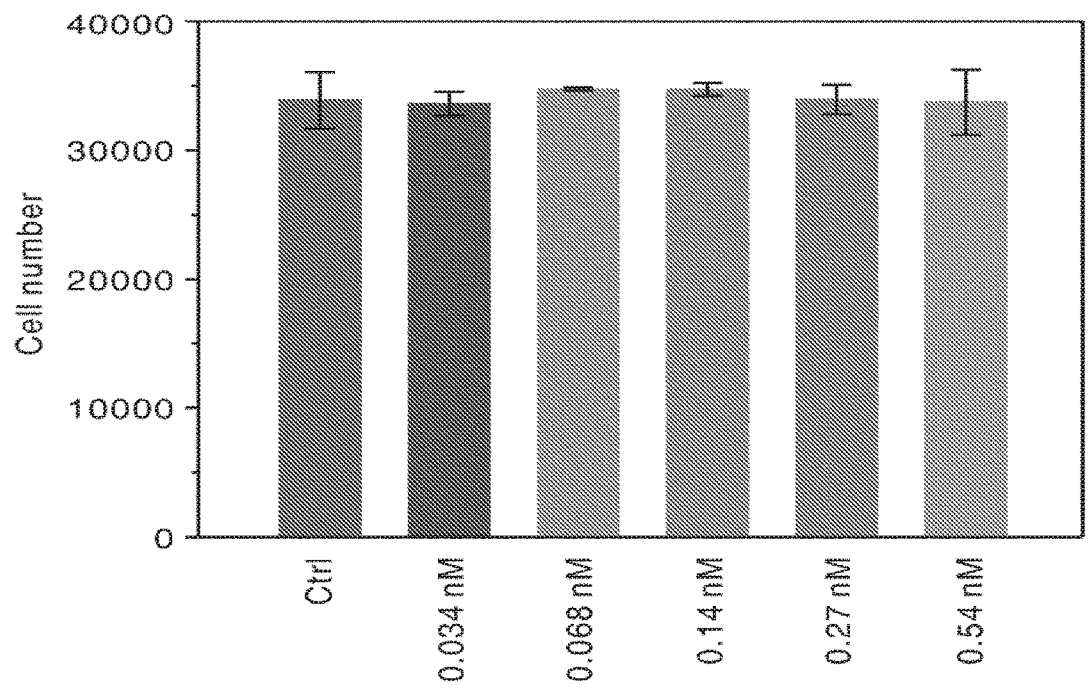
FIG. 2.8

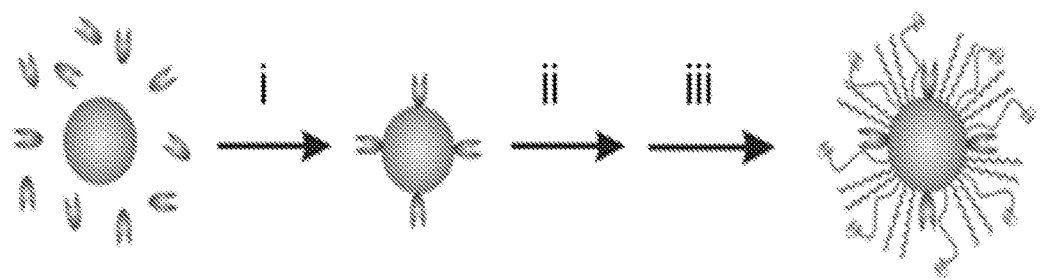
FIG. 3.1
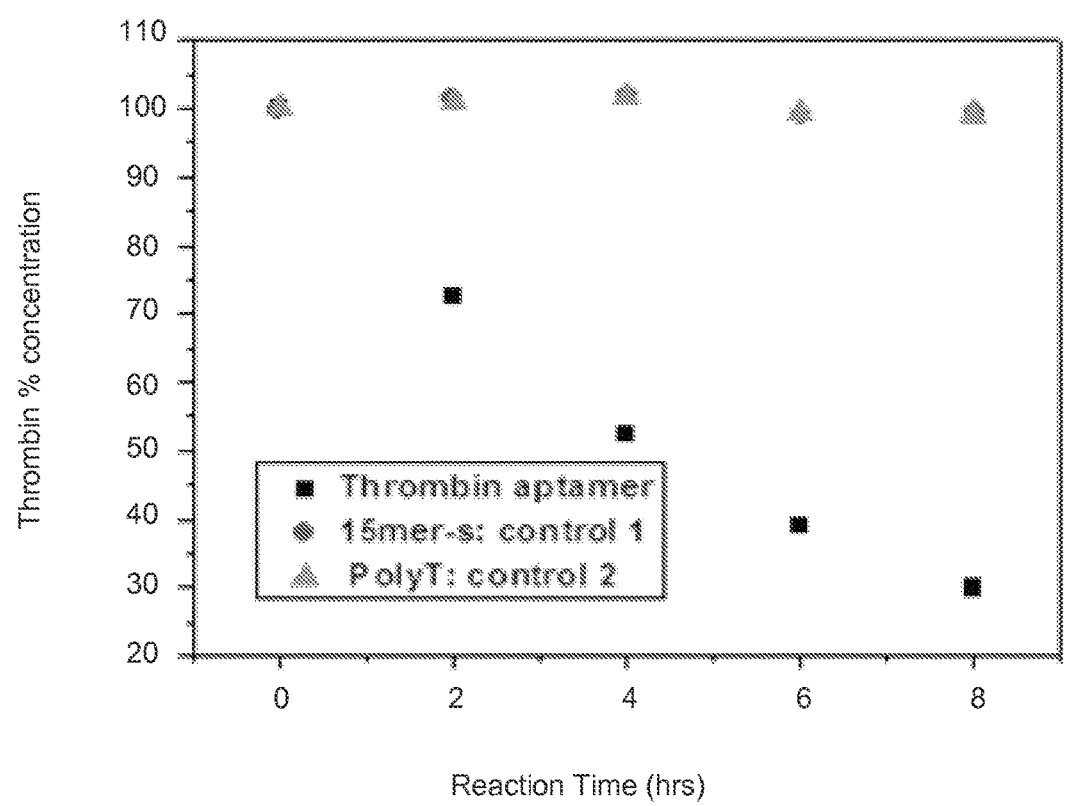
FIG. 3.2

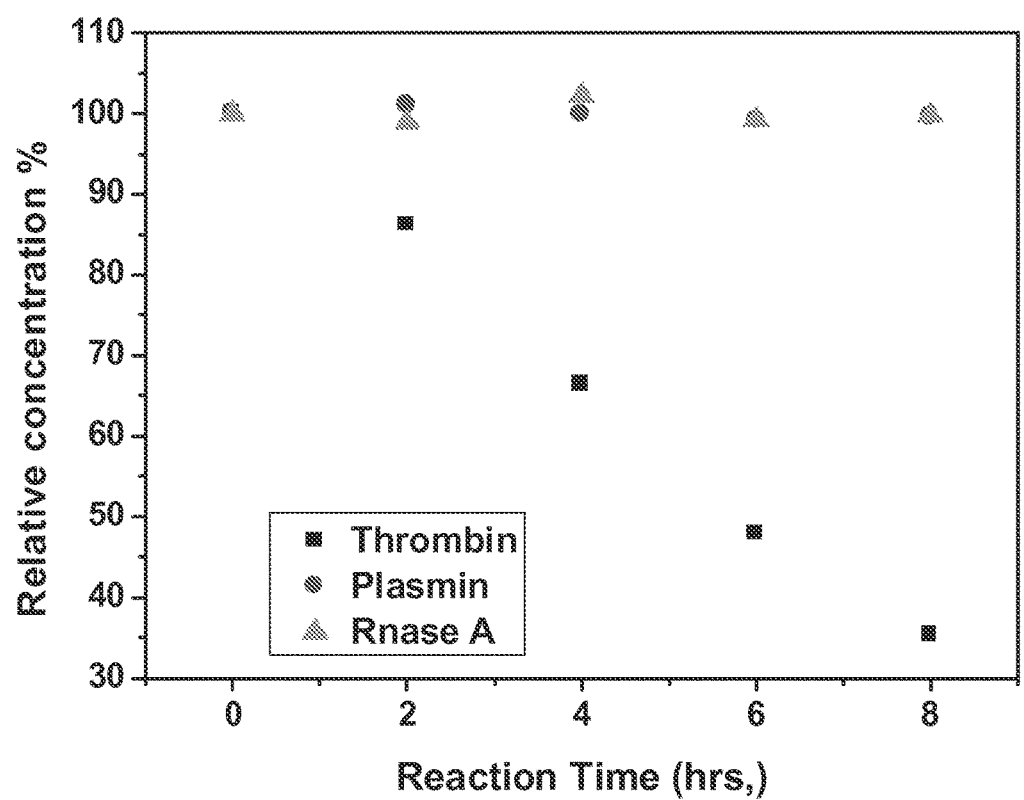
FIG. 3.3

```
                         SEQUENCE LISTING

<160> NUMBER OF SEQ ID NOS: 15

<210> SEQ ID NO 1
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 1
ccttctttaa tggtggctcc at                                              22

<210> SEQ ID NO 2
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 2
ggctcacgga cctttcaca                                                  19

<210> SEQ ID NO 3
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 3
ttagccctag tcacggct                                                   18

<210> SEQ ID NO 4
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 4
tcaccagggc tgctttta                                                   18

<210> SEQ ID NO 5
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 5
ttcacaccca tgacgaaca                                                  19
```

<210> SEQ ID NO 6
<211> LENGTH: 15
<212> TYPE: DNA
<213> ORGANISM: Artificial Sequence
<220> FEATURE:
<223> OTHER INFORMATION: Chemically synthesized single stranded DNA
      oligonucleotide

<400> SEQUENCE: 6
ggttggtgtg gtaaa                                                    15

<210> SEQ ID NO 7
<211> LENGTH: 15
<212> TYPE: DNA
<213> ORGANISM: Artificial Sequence
<220> FEATURE:
<223> OTHER INFORMATION: Chemically synthesized single stranded DNA
      oligonucleotide

<400> SEQUENCE: 7
tttttttttt ttttt                                                    15

<210> SEQ ID NO 8
<211> LENGTH: 18
<212> TYPE: DNA
<213> ORGANISM: Artificial Sequence
<220> FEATURE:
<223> OTHER INFORMATION: Chemically synthesized oligonucleotide

<400> SEQUENCE: 8
ccagagcatc tggcacgt                                                 18

<210> SEQ ID NO 9
<211> LENGTH: 21
<212> TYPE: DNA
<213> ORGANISM: Hepatitis C virus

<400> SEQUENCE: 9
ggucucguag accgtgcacc a                                             21

<210> SEQ ID NO 10
<211> LENGTH: 27
<212> TYPE: DNA
<213> ORGANISM: Artificial Sequence
<220> FEATURE:
<223> OTHER INFORMATION: Chemically synthesized single stranded DNA
      oligonucleotide

<400> SEQUENCE: 10
aaaaaaaaaa aaaaaaaaaa aaaaaaa                                       27

<210> SEQ ID NO 11
<211> LENGTH: 18
<212> TYPE: RNA
<213> ORGANISM: Hepatitis C virus

<400> SEQUENCE: 11
ggucucguag accgugca                                                 18

<210> SEQ ID NO 12
<211> LENGTH: 18
<212> TYPE: DNA
<213> ORGANISM: Artificial Sequence
<220> FEATURE:
<223> OTHER INFORMATION: Chemically synthesized single stranded DNA

```
        oligonucleotide

<400> SEQUENCE: 12
ccagagcatc tggcacgt                                                    18

<210> SEQ ID NO 13
<211> LENGTH: 19
<212> TYPE: RNA
<213> ORGANISM: Artificial Sequence
<220> FEATURE:
<223> OTHER INFORMATION: Chemically synthesized siRNA

<400> SEQUENCE: 13
ggucucguag accgugcac                                                   19

<210> SEQ ID NO 14
<211> LENGTH: 19
<212> TYPE: RNA
<213> ORGANISM: Artificial Sequence
<220> FEATURE:
<223> OTHER INFORMATION: Chemically synthesized siRNA

<400> SEQUENCE: 14
ccagagcauc uggcacgug                                                   19

<210> SEQ ID NO 15
<211> LENGTH: 18
<212> TYPE: DNA
<213> ORGANISM: Artificial Sequence
<220> FEATURE:
<223> OTHER INFORMATION: Chemically synthesized single stranded DNA
       oligonucleotide

<400> SEQUENCE: 15
ccagagcatc tggcacgt                                                    18
```

NANOZYMES, METHODS OF MAKING NANOZYMES, AND METHODS OF USING NANOZYMES

CROSS-REFERENCE TO RELATED APPLICATIONS

This application is the 35 U.S.C. § 371 national stage of PCT application PCT/US2011/32980, filed Apr. 19, 2011, which claims priority to and the benefit of U.S. Provisional Application No. 61/325,922, filed Apr. 20, 2010, both of which are hereby incorporated by reference in their entirety.

FEDERAL SPONSORSHIP

This invention was made with Government support under Contract/Grant No. N00014-06-0911, awarded by the Office of Naval Research. The Government has certain rights in this invention.

BACKGROUND

To date, enzymes have been widely used in medicine. Pancreatic enzymes have been used in digestive disorders since nineteenth century. Most enzymes are used extracellularly for topical applications (e.g., collagenase), removal of toxic substances (e.g., rhodonase), and disorders within blood circulation system (e.g., urokinase). In addition, enzymes have a major potential application in treatment of cancer, e.g., asparagenase in the treatment of lymphocytic leukaemia. However, enzyme applications in medicine are limited by and suffer from following limitations. First, nature enzymes are normally lack of high selectivity to interfere only with disease related metabolic reactions, but also the normal metabolic reaction in a human body. Therefore, enzyme-based drugs (except for those orally administrated digestive enzymes) can lead to significant side effects. Second, enzymes are antigenic, and can elicit immune response in the patient, especially on prolonged use. Third, most enzymes have short effective life in the circulatory system, and very poor stability in endosome during cell entry.

SUMMARY

Embodiments of the present disclosure provides for nanozymes, methods of making nanozymes, methods of using nanozymes, and the like.

One exemplary nanozyme, among others, includes: a nanoparticle, an enzyme, and a recognition moiety, each of the enzyme and the recognition moiety, are attached to the nanoparticle.

Other apparatuses, systems, methods, features, and advantages of this disclosure will be or become apparent to one with skill in the art upon examination of the following drawings and detailed description. It is intended that all such additional apparatuses, systems, methods, features, and advantages be included within this description, be within the scope of this disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1.1 illustrates a scheme of the design of a nanozyme: (1) a nanoparticle scaffold; (2) an enzyme; (3) a recognition moiety; (4) a protection moiety; (5) an inter- and intracellular traffic guiding moiety, and (6) an allosterically functional moiety, where (4), (5), and (6) are optional.

FIG. 1.2 illustrates a scheme of a nanozyme with oligonucleotides as recognition groups and protecting groups: (1) nanoparticle scaffold; (2) enzyme: endoribonucleases (e.g., RNase A and or RNase H) for RNA nanozymes, endodeoxyribonuclease (e.g., DNase I) for DNA nanozymes, and endoproteinase (e.g., proteinase K) for protein nanozymes; (3) ss-oligonucleotides: DNA or LNA for RNA nanozymes, LNA for DNA nanozymes, and DNA or LNA aptamer for protein nanozymes.

FIG. 1.3 illustrates a TEM image of a typical sample of nanozymes.

FIG. 1.4 illustrates a scheme of HCV-specific nanozyme (1), the positive control (2, RNase A), and negative controls (3, 4, 5, and 6).

FIG. 1.5 illustrates a gel electrophoresis analysis of the products from the reaction of (A) HCV RNA, or (B) AAT RNA, with HCV-specific nanozyme (Lane 1); Rnase A (Lane 2), antisense-HCV-DNA oligonucleotide functionalized gold nanoparticles (Lane 3), poly A-functionalized gold nanoparticles (Lane 4), BSPP-functionalized gold nanoparticles (BSPP: bis(p-sulfonatophenyl)-phenylphosphane, Lane 5), and $H_2O$ (Lane 6).

FIG. 1.6 illustrates a real time PCR of HCV infected cells treated with (1) RNase-free water, (2) BSPP-functionalized 13-nm gold nanoparticles, (3) antisense-HCV-DNA oligonucleotide functionalized gold nanoparticles, and HCV-specific nanozyme with RNAse numbers of (4): 3, (5):9, and (6): 15.

FIG. 1.7 illustrates a real time PCR analysis of HCV mRNA from HCV Huh7.5 cells: treated with RNase-free water as control, and 15-RNase HCV-specific nanozyme.

FIG. 1.8 illustrates a real-time PCR analysis of HCV mRNA from the tumor tissue from mice treated with control (RNase-free water) and 15-RNase HCV-specific nanozymes.

FIG. 2.1 illustrates a schematic representation describing the design and function of the nanozyme: (A) shown is an endoribonuclease; (B) nanozyme-bearing DNA oligonucleotides complementary to the sequence at the HCV RNA position (322-339 nt); (C) The sequence of siRNA 331 for silencing HCV; and (D) Gold nanoparticle-DNA oligonucleotides conjugate (Au-DNA), a counterpart of the nanozyme, which does not bear endoribonucleases.

FIG. 2.2 illustrates ribonuclease activity tests for assessing the target selectivity of anti-HCV nanozyme and its ability to resist the degradation of proteinase activities. In these tests, the concentration of nanozymes (or Au-DNA conjugates) is 0.034 nM and that of unbound RNase A is 0.408 nM. The products of these tests were analyzed by using electrophoresis in a 2% formaldehyde agarose gel, and RNA bands were stained by using SYBR Green II. FIG. 2.2(A) illustrates a HCV-RNA segment (nt 1-1149) as the substrate. FIG. 2.2(B) illustrates a 1257-nt AAT RNA segment as the substrate. In a typical proteinase K resistance test, nanozymes (0.034 nM) or particle-free RNase A (0.408 nM) were first incubated with proteinase K (10 nM) in a PBS buffer (pH 7.4) at 37° C. for 1 h. Then the product of this proteinase K treatment was divided into two parts and further incubated with the HCV (or AAT) RNA segment (0.12 µM) in a PBS buffer (11 µL; pH 7.4) at 37° C. for 15 minutes. Abbreviations: Ctrl stands for blank control; and PK for proteinase K.

FIG. 2.3 illustrates a comparison of the efficiencies of RNase H-dependent antisense activity and RNase A-dependent nanozyme function. FIG. 2.3(A) illustrates a gel electrophoresis analysis of RNase H activity tests. These tests were performed in an RNase H buffer (11 µL) with RNase H (1 unit), the HCV RNA segment (0.12 µM), and nanozyme (0.034 nM), or Au-DNA 1 with the conjugates of 0.034 nM, or Au-DNA 2 and 3 with the conjugates of 3.4 nM. The typical RNase reaction time was 15 min, except that a 5-h reaction was performed in the treatment with Au-DNA 3. In addition, a reaction with only the HCV RNA and the anti-HCV nanozyme was carried out as a control to compare the reaction with RNase H. The resulting products were analyzed by using electrophoresis in a 2% formaldehyde agarose gel. Abbreviations: RH for RNase H. FIG. 2.3(B) illustrates a schematic representation describing the steric hindrance effects in the RNase-induced cleavage of RNA/DNA duplexes.

FIG. 2.4 illustrates an anti-HCV effect of the nanozyme in FL-Neo cells. QRT-PCR analysis of HCV RNA expression in the FL-Neo cells treated with the nanozyme, Au-DNA conjugates, and siRNA 331 at varying doses: 0.034 nM (red), 0.14 nM (green), and 0.54 nM (blue). Abbreviations: Ctrl for the blank control treatment with cell growth media, and Lipo for the control treatment with Lipofectamine™ 2000 of the same amount used for siRNA transfection. Each bar presents the mean and standard deviation derived from three independent experiments; Student's t test, NS=non-significance: P=0.062, * for P<0.01, and ** for P=0.00053.

FIG. 2.5 illustrates an anti-HCV nanozyme leading to the inhibition of both the HCV RNA and protein expression in FL-Neo cells. FIG. 2.5(A) illustrates a QRT-PCR analysis of HCV RNA expression in the FL-Neo cells treated with nanozyme, Au-DNA conjugates, and a blank control (the HCV RNA levels were relative to GAPDH). FIG. 2.5(B) illustrates a western blot analysis of NS5A expression in the FL-Neo cells from the treatments above (probed by anti-NS5A antibody and anti-β-actin antibody, respectively). The band intensity (NS5A/β-actin) relative to the control was found to be 0.25±0.02 in the cells treated with nanozymes, while 0.97±0.07 in the cells treated with Au-DNA conjugates. FIG. 2.5(C) illustrates an immunofluorescence analysis of HCV NS5A expression in the individual single FL-Neo cells. The cells were fixed and the HCV NS5A expression level was examined by using fluorescent immunostaining with anti-HCV NS5A antibody and secondary antibody (FITC-labeled goat anti-mouse immunoglobulin G antibody). The nuclei of the cells were stained with DAPI (4',6-diamidino-2-phenylindole) as an internal reference. Mean and standard deviation were derived from three independent experiments.

FIG. 2.6 illustrates an in vivo antiviral effect of the nanozyme in xenotransplanted NOD/SCID mice. QRT-PCR analysis of HCV RNA expression in the xenograft tumors of the mice without treatment (Ctrl) shown as blue squares, those treated with Au-DNA conjugates shown as green dots, the nanozyme shown as red triangles (the HCV RNA levels were relative to GAPDH). Each data point represents an individual mouse, and P-values were calculated using Student's t test.

FIG. 2.7 illustrates a plot of initial reaction rate as a function of RNase A concentration for hydrolysis of cytidine 2':3'-phosphate. The substrate concentration was 0.1 mg/mL.

FIG. 2.8 illustrates the viability and toxicity of FL-Neo cells treated with anti-HCV nanozyme of different concentrations: 0, 0.034, 0.068, 0.14, 0.27, 0.54 nM. Ctrl stands for blank control.

FIG. 3.1 illustrates a scheme of a synthesis of a thrombin-selective nanozyme: (i), loading proteinase K onto the surface of gold nanoparticles; (ii), the loading of recognition group (thrombin-aptamer); and (iii), the loading of protection group (PEG) onto the surface of gold nanoparticles.

FIG. 3.2 illustrates proteinase K assay shows that only a nanozyme with a thrombin aptamer can effectively degrade thrombin.

FIG. 3.3 illustrates a thrombin-selective nanozyme that displays specific degradation of thrombin over Plasmin and Rnase A.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of imaging, chemistry, synthetic organic chemistry, biochemistry, biology, molecular biology, microbiology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

By "administration" is meant introducing a nanozyme of the present disclosure into a host. Any route of administration, such as intravenous, oral, topical, subcutaneous, peritoneal, intraarterial, inhalation, vaginal, rectal, nasal, introduction into the cerebrospinal fluid, or instillation into body compartments can be used.

As used herein, the term "host", "subject", or "patient" includes humans, mammals (e.g., cats, dogs, horses, etc.), and the like. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. The term "living host" refers to host noted above that are alive. The term "living host" refers to the entire host and not just a part excised (e.g., a liver or other organ) from the living host.

The term "sample" can refer to a tissue sample, cell sample, a fluid sample, and the like. The sample may be taken from a host. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue. In the present disclosure, the source of the sample is not critical.

The term "detectable" refers to the ability to detect a signal over the background signal.

The term "detectable signal" is a signal derived from non-invasive imaging techniques such as, but not limited to, magnetic resonance imaging (MRI). The detectable signal is detectable and distinguishable from other background signals that may be generated from the host. In other words, there is a measurable and statistically significant difference (e.g., a statistically significant difference is enough of a difference to distinguish among the detectable signal and the background, such as about 1%, 3%, 5%, 10%, 15%, 20%, 25%, 30%, or 40% or more difference between the detectable signal and the background depending on the circumstances) between detectable signal and the background. Standards and/or calibration curves can be used to determine the relative intensity of the acoustic detectable signal and/or the background.

General Discussion

Embodiments of the present disclosure provides for nanozymes, methods of making nanozymes, methods of using nanozymes, and the like. One or more of the embodiments of the present disclosure may be advantageous because they can be designed to be selective, may not produce an elicit immune response, can have an extended life time, and/or can be stabile for longer periods of time, relative to other enzyme based products. Embodiments of the present disclosure can be used to image, detect, study, monitor (e.g., survival), evaluate, and/or treat, a condition or disease using an embodiment of the nanozyme. Additional details are described in the Examples.

In an embodiment, the nanozyme can include a nanoparticle, an enzyme, and a recognition moiety. Each of the enzyme and the recognition moiety are attached (e.g., directly or indirectly via a linker (e.g., compound or protein) or the like) to the nanoparticle. In an embodiment, the nanozyme can include two or more types (e.g., have different functions) of enzymes and/or recognition moieties. In an embodiment, the nanozyme can also include a protection moiety, an inter- and intra-cellular traffic guiding moiety, and/or an allosterically functional moiety.

The nanoparticle can function as a scaffold for the other components to attach. In an embodiment, the nanoparticle can also function as a detectable nanoparticle (e.g., that has or is able to produce a detectable signal) that can be detected using imaging methods such as fluorescence, MRI, darkfield optical microscopy, Raman microscopy, and a combination thereof. In an embodiment, the nanoparticle can include, but is not limited to, quantum dots (e.g., II-VI, III-V, IV-VI semiconductor quantum dots), metal nanoparticles, magnetic nanoparticles, metal oxide nanoparticles, heterogeneous dimer, trimer, oligomer, and polymer nanoparticles, composite organic/inorganic nanoparticles, single walled nanotubes, multiwalled nanotubes, and graphene. In an embodiment, the nanoparticles can be isotropic shaped such as spherical, cubic, tetrahedron, polyhedron, or anisotropic shaped such as a nanoplate, a nanorod, a nanowire, and a nanoprism. The dimension of the nanoparticle can be about 1 to 5000 nm, about 1 to 1000 nm, or about 1 to 500 nm, in diameter for spherical or near spherical nanoparticles (or the longest distance along a cross-section of the nanoparticle). The nanoparticle can include a number of types of nanoparticles such as, but not limited to, semiconductor, metal (e.g., gold, silver, copper, tungsten, platinum, palladium, titanium, and the like), and metal oxide nanoparticles (such as $In_2O_3$, $ZnO$, $Ga_2O_3$, $Co_2O_3$, $NiO$, $WO_3$, and $MoO_3$), metalloid and metalloid oxide nanoparticles, the lanthanide series metal nanoparticles or oxides thereof, and combinations thereof. In an embodiment, the magnetic nanoparticles (e.g., those having magnetic properties) can include, but are not limited to, iron oxide nanoparticles (e.g., $Fe_2O_3$, and $Fe_3O_4$), iron composite nanoparticles such as Fe and FePt nanoparticles, and lanthanide containing nanoparticles such as Co—Sm nanoparticles.

The enzyme can function to act upon a nucleotide (e.g., DNA, RNA, or smaller nucleotide) or a peptide (e.g., protein). In an embodiment, the enzyme functions include hydrolysis, methylation, de-methylation, phosphorylation, de-phosphorylation, ubiquitylation, oxidation, reduction, nucleic acid editing, condensation, or other like enzymatic modifications for DNA, RNA, proteins, peptides, oligosuccharides, polysaccharides, or small molecules such as neuron transmitters. In an embodiment, the enzyme does not react with the recognition moiety and the protecting moiety when attached to the nanoparticle or does not substantially react (e.g., can react at a rate with the recognition moiety and/or the protecting moiety so that the nanozyme can be used to accomplish the desired goals and/or perform the desired function(s) of the nanozyme) with the recognition moiety and the protecting moiety when attached to the nanoparticle.

In an embodiment, the enzyme can include endoribonucleases, endodeoxyribonuclease, endoproteinase, or a combination thereof. In an embodiment, the endoribonuclease can include: RNase A, RNase III, RNase H, RNase P, or RNase T1. In an embodiment, the endodeoxyribonuclease can include: deoxyribonuclease II, deoxyribonuclease IV, restriction enzyme, and UvrABC endonuclease. In an embodiment, the endoproteinase can include: proteinase K, trypsin, chymotrypsin, elastase, thermolysin, pepsin, and endopeptidase V8. In an embodiment, the nanozyme can include 1 to 200 enzymes attached to the nanoparticle.

In an embodiment, the recognition moiety can function to cause the nanoenzyme to interact with a molecule(s). In an embodiment, the recognition moiety can have an affinity for a cell, a tissue, a protein, DNA, RNA, an antibody, an antigen, and the like, that may be associated with a condition, disease, or related biological event, of interest. In particular, the recognition moiety can function to target specific DNA, RNA, and/or proteins of interest. The recognition moiety can include, but is not limited to, polypeptides (e.g., proteins such as, but not limited to, antibodies (monoclonal or polyclonal)), antigens, nucleic acids (both monomeric and oligomeric), polysaccharides, sugars, fatty acids, steroids, purines, pyrimidines, ligands, aptamers, small molecules, ligands, or combinations thereof, that have an affinity for a condition, disease, or related biological event or other chemical, biochemical, and/or biological events of the condition, disease, or biological event. In an embodiment, the recognition moiety can include: sequence-specific DNA oligonucleotides, locked nucleic acids (LNA), and peptide nucleic acids (PNA), antibodies, and small molecule protein receptors. In an embodiment, the nanozyme can include 1 to 2000 recognition moieties attached to the nanoparticle. In an embodiment, the recognition moiety can also include the function(s) of the protecting moiety, and/or inter- and intracellular traffic guiding moiety so that the recognition moiety has multiple (e.g., ternary) functions. The function(s) of the protecting moiety are described herein.

In an embodiment, the nanozyme can also include a protecting moiety. The protecting moiety is attached (e.g., directly or indirectly via a linker (e.g., compound or protein) or the like) to the nanoparticle. In an embodiment, the protecting moiety can function to control the intracellular stability, dispersibility, cell-uptake efficiency, and/or selective cell-entry efficiency. Alternatively or in addition, the protecting moiety can substantially reduce (e.g., reduce by about 70%, about 80%, about 90%, about 95%, or about 99% relative to not including the protecting group) or eliminate the toxicity of the nanozyme and/or substantially reduce (e.g., reduce by about 70%, about 80%, about 90%, about 95%, or about 99% relative to not including the protecting group) or eliminate the immunogenicity of the nanozyme, or a combination both. In an embodiment, the protecting moiety can reduce (e.g., reduce by about 70%, about 80%, about 90%, about 95%, or about 99% relative to not including the protecting group), or eliminate non-target molecules from approaching the enzymes of the nanoenzyme, and can protect the enzyme moiety of the nanozyme from degradation by enzymes (e.g., proteinases).

In an embodiment, the protecting moiety can include: DNA oligonucleotides, locked nucleic acids (LNA), peptide nucleic acid (PNA), poly(ethylene glycol) (PEG), poly(vinyl alcohol) (PVA), poly(acrylic acid) (PAA), poly(propylene furmarate-co-ethylenee glycol) (P(PF-co-EG)), polyacrylamide, polypeptides, poly-N-substituted glycine oligomers (polypeptoids), hyaluronic acid (HA), alginate, chitosan, agarose, collagen, fibrin, gelatin, dextran, and any combination thereof, as well as derivatives of each of these ligands and the like. In an embodiment, the nanozyme can include 1 to 2000 protecting moieties attached to the nanoparticle. In an embodiment, the nanozyme can include two or more types (e.g., have different functions) of enzymes, protecting moieties, and/or recognitions moieties.

In an embodiment, the inter- and intra-cellular traffic guiding moiety can guide a nanozyme into specific organs (such as liver), cell types (such as Hepatocyte), sub-cellular organelles, and nucleus. In an embodiment, the inter- and intra-cellular traffic guiding moiety can include DNA oligonucleotides, locked nucleic acids (LNA), peptide nucleic acid (PNA), cyclodextrin, polymers, TransFectin, and any combination thereof, as well as derivatives of each of these ligands and the like. In an embodiment, the nanozyme can include 1 to 2000 inter- and intra-cellular traffic guiding moiety attached to the nanoparticle. In an embodiment, the nanozyme can include two or more types (e.g., have different functions) of enzymes, protecting moieties, and/or recognitions moieties, and/or inter- and intra-cellular traffic guiding moieties.

In addition, the allosterically functional moiety can also be attached onto this nanozyme. The allosterically functional moiety enables the nanozyme to have an on/off switch in response to chosen allosteric effectors such as specific products or byproducts (e.g., glucose) in disease-associated metabolism pathways. In an embodiment, the allosterically functional moiety can include DNA, RNA, peptide nucleic acid (PNA), locked nucleic acid (LNA), a peptide, a protein, a sugar, a lipid, a small molecular receptor such as biotin, cyclodextrin, a polymer, TransFectin, and a combination thereof, as well as derivatives of each of these moieties and the like.

In addition to the enzyme, the recognition moiety, the protecting moiety, and/or inter- and intra-cellular traffic guiding moieties, the nanozyme can include a therapeutic agent such as a drug that can be used to treat the disease or condition of interest.

Kits

This disclosure encompasses kits, which include, but are not limited to, nanozymes, and directions (written instructions for their use). The components of the nanozyme can be tailored to the particular disease, condition, or even being studied and/or treated. The kit can further include appropriate buffers and reagents known in the art for administering various combinations of the components listed above to the host cell or host organism.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Embodiments of the present disclosure provide methods of the synthesis of nanozymes nanoparticle-based enzymes, which is a new class of biological catalysts) for biotechnology and therapeutic applications.

To date, enzymes have been widely used in medicine. Pancreatic enzymes have been used in digestive disorders since nineteenth century.[1,2] Most enzymes are used extracellularly for topical applications (e.g., collagenase), removal of toxic substances (e.g., rhodonase), and disorders within blood circulation system (e.g., urokinase). In addition, enzymes have a major potential application in treatment of cancer, e.g., asparagenase in the treatment of lymphocytic leukaemia.[1,2] However, enzyme applications in medicine are limited by and suffer from following limitations. First, nature enzymes normally lack of high selectivity to interfere only with disease related metabolic reactions, but also the normal metabolic reaction in a human body. Therefore, enzyme-based drugs (except for those orally administrated digestive enzymes) can lead to significant side effects. Second, enzymes are antigenic, and can elicit immune response in the patient, especially on prolonged use. Third, most enzymes have short effective life in the circulatory system, and very poor stability in endosome during cell entry.[3]

To overcome these limitations, we discovered a nanozyme technology. A nanozyme, in general, can contain five components: a nanoparticle, one or more types of enzymes with specific functions, recognition groups, protecting ligands, and/or inter- and intra-cellular traffic guiding moiety ligands (FIG. 1.1). The nanoparticle component is the scaffold of a nanozyme, providing a large surface area to hold enzymes and recognition groups at close proximity. The enzymes (natural or bio-engineered enzymes) are the main functional groups in nanozyme, which functions can include, but is not limited to, hydrolysis, methylation and de-methylation, phosphorylation, and de-phosphorylation, and ubiquitylation.[4] In an embodiment, the design of a nanozyme is that the enzymes should not react with the recognition groups and protecting groups on the nanozyme. The recognition groups could selectively bind to targets (e.g., such as mRNA, Protein, or DNA) of interest, and bring them to the nearby enzymes for reaction, and therefore, well-designed recognition groups can make nanozymes exhibit extraordinary high target selectivity. The protecting ligands control the intracellular stability and dispersibility of nanozymes. Together with the recognition groups, the protecting ligands can also prevent non-target molecules approaching to the enzymes on a nanozyme, and resulting in additional selectivity for the nanozyme. With further functionalization, the protecting ligands can make nanozymes have (1) enhanced cell-uptake efficiency, (2) selective cell-entry efficiency, (3) low cytotoxicity, and (4) weak immunogenicity.[5] In addition, this platform will allow loading drug molecules onto nanozymes for achieving multiple therapeutic effects. Moreover, nanozymes can be used as biological image contrast agents for transmission electron microscope (TEM),[6] fluorescence imaging, and/or MRI.[7] Furthermore, because of their large hydrodynamic sizes (~1-100 nm), nanozyme can passively target cancers via EPR (i.e., enhanced permeability and retention) effects.[8]

To demonstrate the function of nanozymes, we have designed and fabricated three major types of nanozymes for different types of targets of interest: RNA, DNA, and proteins (FIG. 1.2). Such a nanozyme herein possesses a nanoparticle, one or more types of hydrolases, and single-stranded (ss) oligonucleotides (DNA or locked nucleic acids: LNA, FIG. 1.2). The nanoparticle component, is the scaffold of this nanozyme, determines its size and shape, and allows nanozymes to be used as biological imaging agents for TEM, fluorescence imaging, and/or MRI. We use endoribonucleases (e.g., RNase A and or RNase H) as hydrolase for RNA targets, endodeoxyribonuclease (e.g., DNase I) for DNA target, and endoproteinase (e.g., proteinase K) for protein targets (FIG. 1.2). These enzymes are endohydrolases without sequence selectivity. With the recognition groups at close proximity on a nanozyme, these endohydrolases can selectively degrade their target with sequence specificity. Single-stranded oligonucleotides work as both the recognition groups and protecting ligands in the nanozyme (FIGS. 1.1 and 1.2). For DNA targets, we use LNA to modify nanozymes, because such oligonucleotides cannot be degraded by the DNase I on nanozymes. For protein targets, we use DNA or LNA aptamer oligonucleotide as the recognition group of the nanozyme. In addition, single-stranded (ss) oligonucleotides also have the functions as protecting ligands and inter- and intra-cellular traffic guiding moiety ligands.

Nanozymes for RNA targets can be used as a class of novel agents for intercellular post-transcriptional gene regulation. Such a nanozyme is a synthetic analog of the activated RISC(RNA-induced silencing complex) in RNA interference.[9-11] An activated RISC can sequence-selectively cleave mRNAs of interest, and prevent them from producing a protein.[10,11] RNA interference has an important role in defending cells against parasitic genes—viruses and transposons—but also in directing development as well as gene expression in general.[11] Small interfering RNA (siRNA) technology has a potential to become a novel therapeutic approach for many human diseases.[12] The challenge for a successful application is the delivery and efficiency of siRNA. In addition, siRNA technology utilizes cellular machines such as RICS complex to achieve therapeutic effects, and such a therapeutic process can potentially interfere with the normal cell development that are also based on these cellular machines, and result in toxicity and side effects.[13] These challenges can be overcome with nanozyme technology because of the novel properties of nanozymes. Moreover, nanozymes can cleave/degrade the mRNAs of interest using their own RNase components, without the need of cellular machinery.

To demonstrate the use of nanozyme for post-transcriptional gene regulation, we have chosen the mRNA of hepatitis C virus (HCV) as a target. HCV infection is a major cause of liver cancer.[14,15] HCV is a plus-stranded RNA virus with a genome size of 9.6 kb.[16] The virus replicates through a negative strand RNA intermediate without evidence of DNA formation. The virus is classified as the distinct genus "Hepacivirus" in the family of Flaviviridae.[17] HCV infects 170 million people worldwide.[14,15] It causes significant liver disease ranging from chronic hepatitis to cirrhosis and hepatocellular carcinoma.[18] In contrast to most other viral infections, the hallmark of HCV viral infection is that the majority of patients (up to 80%) will develop chronic infection after viral exposure.[19] HCV infection is the leading etiology for liver cancer in the United States. The cleavage or degradation of the mRNA of HCV can block the pathway of the virus replication, and lead to a cure for HCV infection.

In the design of HCV-specific nanozyme, the sequence of ssDNA oligonucleotides is chosen according to the antisense sequence of the 5' nontranslated (NRT) region of HCV mRNA (FIG. 1.4).[20] A typical synthesis of HCV-specific nanozymes includes two steps, in which RNase-free water was used as the solvent for all the chemicals and reagents. In the first step, a sodium carbonate solution (100 mM) was used to adjust a 13-nm gold nanoparticle solution to pH9.6 (11 nM of gold nanoparticles, 0.90 mL). A solution of RNase-A (5 µM, 100 µL) was added in the gold particle solution. The resulting solution was shaken vigorously for 45 min, resulting in the formation of RNase-gold nanoparticle conjugates. Then, in the second step, a solution of ssDNA oligonucleotides (0.1 mM, 34 µL) was added to the RNase-gold nanoparticle conjugate solution. After the resulting solution is shaken for 8 h, a NaCl solution (1 M, 35.7 µL) was added to make the solution with a NaCl concentration of 0.05 M. Then the solution was continuously shaken for another 8 h, and the NaCl concentration of the solution was increased to 0.10 M by adding NaCl solution (1 M, 38.2 µL). After the resulting solution is shaken for another 8 h, its NaCl concentration was increased to 0.20 M. Then the solution was shaken for another 8 h, its NaCl concentration was increased to 0.30 M. After the solution was shaken for 8 h, resulting HCV-specific nanozyme was precipitated from the solution using a centrifuge (14000 g, for 20 min). Oily nanozyme precipitate was dispersed in RNase-free water (pH 7.2) for use.

A typical nanozyme solution exhibits a narrow extinction peak at 526 nm, which originates from the 13-nm gold nanoparticle scaffolds. This nanozyme solution is extremely stable, and no measurable change in its extinction spectrum was observed more than half year. A transmission electron microscope (TEM) image of the typical sample shows that nanozymes are highly monodispersed particles of 13 nm in diameter, with a relative standard deviation of 7% (FIG. 1.3). The average number of RNase loaded on a nanozyme is 15 with a relative standard deviation of 9%. In addition, we found that the average number of RNase A is nearly linearly proportion to the molar ratio of RNase-A added and gold nanoparticles in the first step of the nanozyme synthesis. By tuning this molar ratio, we have prepared nanozyme with an average number of RNase of 3, 6 and 9, respectively. On a nanozyme, the average number of ssDNA oligonucleotides is inversely related to the average number of RNase-A: the more the RNase-A is associated to the less of the ssDNA oligonucleotides. There are about 77 oligonucleotides on a nanozyme with 15 RNase-A molecules.

To evaluate the target selectivity of nanozymes, we used 15-RNase HCV-specific nanozyme as the model nanozyme, RNase A as the positive control, and RNase-free water as the negative control. We chose two types of in vitro transcribed RNA as targets: HCV (JFH-1 strain) RNA as the target, and RNA of Alpha-1 antitrypsin (AAT) as the control target. In a typical experiment, a RNA solution (1 µg/30 µL, pH 7.00) was mixed with a solution of nanozyme (or a control), and the concentration of nanozyme (or control) in the resulting solution is 0.04 nM. This mixture was incubated at 37° C. for 30 min. For the same type of RNA target (HCV RNA, or AAT RNA), the tests of nanozyme activity, positive and negative controls were carried out nearly simultaneously, and the RNase concentration in the positive control test is identical to that in the test with nanozyme and the control nanozyme (FIG. 1.4). After incubation at 37° C., the reaction mixtures in these three tests were loaded on to a non-denaturing agarose gel, and electrophoresed at 5-6 V/cm for about 30 mins. Then the gel was stained with ethidium bromide, and visualized under a UV transilluminator (FIG. 1.5).

Gel electrophoresis analysis demonstrates that the HCV-specific nanozyme exhibits extraordinarily high target selectivity. HCV RNA in the negative control was seen as a narrow band, while the product of the reaction of HCV RNA and HCV-specific nanoizyme was seen only as a broad band (of ~220-40 bps). This result clearly shows that HCV-RNA molecules were degraded into shorter strands by HCV-specific nanozyme (FIG. 1.5A—Lane 1). In contrast, HCV-specific nanozyme exhibits nearly no enzymatic activity in the reaction with AAT RNA substrates, showing that HCV-specific nanozyme only catalyzes the hydrolysis of RNA targets with a complementary sequence to the ssDNA oligonucleotides of this nanozyme (FIG. 1.5B—Lane 1). Moreover, HCV-specific nanozymes react with HCV RNA in a different pathway from the reaction of free-RNase and HCV. The reaction of free-RNase and HCV yields a broad and smeared band (FIG. 1.5A—Lane 2), while the reaction of HCV RNA and HCV-specific nanoizyme yields a broad band (of ~220-40 bps, FIG. 1.5A—Lane 2). In addition, free-RNase also non-selectively degraded AAT RNA (FIG. 1.5B—lane). Furthermore, the controls of using antisense-HCV-DNA oligonucleotide functionalized gold nanoparticles, poly A-functionalized gold nanoparticles, BSPP-functionalized gold nanoparticles (BSPP: bis(p- sulfonatophenyl)-phenylphosphane), and H$_2$O show no reactivity with either HCV and AAT RNA. Taken together, these results unambiguously demonstrate that HCV-specific RNA have sequence specificity for its target—HCV RNA, and this RNA sequence specificity should originate from the cooperativity of its three components: nanoparticle scaffold, RNase—the enzyme, and oligonucleotide—the recognition group.

We attribute this target selectivity to the effects of the ssDNA oligonucleotides on the surface of nanozymes (FIG. 1.4). On one hand, the densely packed ssDNA oligonucleotides on nanozymes can block the access of non-complementary RNA molecules to the RNases via steric hindrance and repulsive coulomb interactions. In addition, these negative charged ssDNA oligonucleotides can block the positive-charged activation sites of the RNases, and further prevent the interaction of non-complementary RNA with these RNases. On the other hand, these ssDNA oligonucleotides bind HCV RNA through hybridization, and bring these target RNA molecules to the close proximity of the RNases nearby, leading to the cleavage and/or degradation of these RNA molecules.

To study the effect of HCV-specific nanozymes against HCV replication in cell culture, we chose FLneo cells as a model system. In a typical experiment, FLneo cells were seeded in 6-well plates and incubated in DMEM culture medium overnight. Controls (control 1: RNase-free water, control 2: BSPP-functionalized gold nanoparticles, and control 3: antisense-HCV-DNA oligonucleotide functionalized gold nanoparticles), and HCV-specific nanozymes with number of RNases of 3, 9 and 15 was incubated with the HCV-infected cells (FIG. 1.6). After 24 h incubation, these cells were treated with the controls and nanozymes again. After 72 h of treatment, the cells were harvested for viral RNA assay using real-time PCR. No measurable cell death was observed during the nanozyme treatment. Using human glyceraldehyde-3-phosphate dehydrogenase gene (GAPDH) as internal reference, we obtained the viral copy numbers per sample from real-time PCR analysis. BSPP-functionalized gold nanoparticles (control 2) and antisense-HCV-DNA oligonucleotide functionalized gold nanoparticles (control 3) show a barely measurable inhibition effect on HCV replication (FIG. 1.6). In contrast, nanozymes exhibit a significant inhibition effect on HCV replication, and the inhibition efficiency is dependent upon the number of RNases on nanozymes (FIG. 1.6). The more the RNases leads to the large the inhibition effect. Significantly, 15-Rnase nanozymes blocked 55% HCV replication.

More importantly, HCV-specific nanozyme prevent Huh7.5 cells from HCV infection. In a typical experiment, Huh7.5 cells were cultured in 6-well plates, and treated with 12-Rnase nanozymes twice during 24 h. Then the cells were incubated with HCV for 24 h, and then the cells were washed with PBS and cultured in DMEM medium for another 4 days. The cells were harvested for viral RNA assay using real-time PCR. Using host-keeping gene GADPH as internal reference, we obtained the viral copy numbers per sample from real-time PCR analysis (FIG. 1.7). Significantly, the cells treated with nanozymes showed 46% less HCV infection than those treated with the control (RNase-free water, FIG. 1.7).

Furthermore, HCV-specific nanozyme exhibit inhibition effects on HCV replication in a mouse model. A typical experiment was conducted using an orthotopic human liver cancer mouse model. The model is based on the observation that inactivation of endogenous liver cells from cell division will allow tumor cells to repopulate in a mouse liver after partial hepatectomy (50-70% liver tissue removal).[21] Two experimental groups were used in the test (treatments with and without 15-RNase nanozyme). Six mice were used for each experimental group. After tumor cells grew evidently, the mice were treated with nanozyme and control solutions every two days for one week. Then the mice were sacrificed, and cancer tissue was harvested for real-time PCR analysis. Using GAPDH as internal reference, we obtained the viral copy numbers per sample from real-time PCR analysis (FIG. 1.8). Significantly, nanozyme inhibited the replication of HCV by 9% as compared with that in the control group.

In conclusion, we have discovered a nanozyme technology. The results from our experiments demonstrate that nanozymes exhibit high target selectivity and high enzymatic activity in vitro, in cell culture, and in animal model. Nanozymes have the potential to become a new class of general therapeutic agents for diseases such as viral infection and cancer. In addition, nanozymes are a new class of catalysts with the potential to be a general tool for fundamental biology studies such as gene knockdown and functional genomics, and to a new general tool for biotechnology in agriculture such as the engineering of food plants that produce lower levels of natural plant toxins.[22]

Reference for Example 1, Which are Included Herein by Reference:

1. Cassileth, Barrie R. "Enzyme Therapy." In The Alternative Medicine Handbook. New York: W.W. Norton & Company, 1998.
2. Cichoke, Anthony J. "Enzymes & Enzyme Therapy: How to Jump-Start Your Way to Lifelong Good Health," Chicago: Keats Publishing, 2000.
3. Smit, M J; Beekhuis, H; Duursma, A M; Bouma, J M; Gruber, M., *Clinical Chemistry* 1988, 34, 2475-2480.
4. Bairoch A. *Nucleic Acids Res* 2000, 28, 304.
5. Rosi N L, Giljohann D A, Thaxton C S, Lytton-Jean A K, Han M S, Mirkin C A. *Science* 2006; 312, 1027-30.
6. Chan W C, Nie S. *Science* 1998, 281, 2016-8.
7. Lee, J. H.; Huh, Y. M.; Jun Y W, Seo, J. W.; Jang, J. T.; Song, H. T.; Kim, S.; Cho, E. J.; Yoon, H. G.; Suh, J. S.; Cheon, *J. Nat Med* 2007, 13, 95-9.
8. Brigger I, Dubernet C, Couvreur P. *Adv. Drug. Deliv. Rev.* 2002; 54:631-51
9. Fire A, Xu S, Montgomery M, Kostas S, Driver S, Mello C., *Nature* 1998, 391, 806.
10. Macrae I, Zhou K, Li F, Repic A, Brooks A, Cande W, Adams P, Doudna J, *Science* 2006, 311, 195.
11. Bagasra O, Prilliman K R *J. Mol. Histol.* 2004, 35, 545.
12. Kandel, E. S. *Biomolecular Engineering* 2006, 23, 17.
13. Gartel, A. L.; Grimm D, Streetz K L, Jopling C L, Storm T A, Pandey K, Davis C R, Marion P, Salazar F, Kay M A. *Nature* 2006, 441, 537.
14. Alter M J, Kruszon-Moran D, Nainan O V, McQuillan G M, Gao F, Moyer L A, Kaslow R A, Margolis H S. The prevalence of hepatitis C virus infection in the United States, 1988 through 1994. *N Engl J Med* 1999, 341, 556-62.
15. Anonymous. Global survillence and control of hepatitis C. *J. Viral Hepat.* 1999, 6, 35.
16. Choo Q L, Kuo G, Weiner A J, Overby L R, Bradley D W, *Science* 1989, 244, 359-62.
17. Poynard T, Yuen M F, Ratziu V, Lai C L. Viral hepatitis C. *Lancet* 2003, 362, 2095-100.
18. Liang, T. J.; Rehermann, B.; Seeff, L. B.; Hoofnagle, J. H. *Ann Intern Med* 2000, 132, 296.
19. Cerny A, Chisari F V. *Hepatology* 1999, 30, 595.
20. Jopling C. L.; Yi, M.; Lancester, A. M.; Lemon, S. M.; Sarnow, P.; *Science* 2005, 309, 1577.

21. Witek, R. P.; Fisher S H, Petersen B. E. *Cell Transplant* 2005, 14, 41.
22. Siritunga, D, Sayre, R. *Planta* 2003, 217, 367.

Example 2

Brief Introduction

RNA silencing is a fundamental gene regulation mechanism in the cell. Here we report the synthesis of a nanoparticle complex that can effectively mimic the function of an active RNA-induced gene silencing complex—the cellular machinery that mediates the RNA interference (RNAi) pathways. Our results show that this nanoparticle complex displayed potent antiviral activity against hepatitis C virus in cultured cells and a mouse model; we observed a 99.7% decrease in virus RNA levels in mice treated with this complex. Since the function of the nanoparticle complex does not rely on cellular RNAi machinery, the RNA silencing approach herein complements those RNAi methods and has the potential to become a useful tool for functional genomics and for combating protein expression-related diseases such as viral infections and cancers.

Introduction and Discussion

The use of RNA interference (RNAi) to control gene expression has emerged as a basic experimental tool for studying gene function and biological pathways in living cells and living organisms including plants and animals (1-3). RNAi is a sequence-specific RNA silencing mechanism that is mediated by small RNAs—such as small interference RNAs (siRNAs)—through the action of an endonuclease-containing protein complex known as RNA-induced silencing complex (RISC). Exogenous siRNA-based RNAi techniques have the potential to provide powerful therapeutic approaches for human diseases, and a number of siRNA-based therapies are currently being evaluated in clinical trials (4-6). However, because the therapeutic effects of siRNA drugs depend on cellular RNAi machineries, this therapeutic intervention can perturb natural cellular gene regulation pathways mediated by endogenous microRNAs that also rely on these cellular machineries, thus resulting in potential toxicity and side effects (4, 7, 8). In addition, the therapeutic effects of siRNA can be inhibited by RNAi suppressors that are encoded by pathogenic human viruses such as hepatitis C virus (HCV) and HIV (9, 10). Moreover, delivery of siRNA drugs into cells or tissues poses another major challenge to its clinical application (4, 8).

It this example an approach with the potential to overcome the difficulties associated with the use of siRNA-based drugs is presented. This approach utilizes a simple synthetic complex—including of a nanoparticle, non-sequence specific endoribonucleases, and single-stranded DNA oligonucleotides—that can effectively mimic the RNA-silencing function of an active RISC in the RNAi pathway: this nanoparticle-based active RNA silencing complex (a type of nanozymenanozyme) enzymatically cleaves messenger RNAs containing specific sequences (FIG. 2.1). Thus far, nanoparticles have been extensively developed for biomedical imaging (11-15) and drug delivery applications (16-18), and nanoparticle-based delivery systems have demonstrated the remarkable ability to increase the selectivity of drugs toward cancer cells while reducing their toxicity to normal cells (16, 17). Such nanoparticle-based delivery systems also enable detailed tracking of the drug locations within a patient's body by using simultaneous biomedical imaging techniques (16, 17, 19). In this study, a nanoparticle is used as the backbone of nanozyme, providing a large surface area to hold endoribonucleases and DNA oligonucleotides at close proximity. Endoribonucleases are the catalytically active components of nanozyme, while DNA oligonucleotides function as the components responsible for target recognition via Watson-Crick base pairing and direct the endoribonucleases to cleave target RNAs that contain complementary sequences. Owing to their low toxicity and unique surface chemical properties for alkylthiol functionalization (20-22), gold nanoparticles are chosen to construct nanozymes. RNase A is used as the endoribonuclease component because it is one of the most robust and active endoribonucleases for non-sequence specific degradation of single-stranded RNAs, which have routinely been used for the removal of RNA contamination from DNA preparations as well as the removal of unhybridized regions of RNA from DNA/RNA or RNA/RNA hybrids (3).

HCV was chosen as a model system to evaluate the function and efficacy of nanozyme for silencing gene expression and suppressing viral replication. HCV is a major cause of liver diseases such as chronic hepatitis, cirrhosis and liver cancers (23). More than 170 million people are infected by HCV worldwide (24). Current interferon-based therapy only results in sustained virus clearance in around 50% patients, while the therapy is not HCV-virus specific and has significant side effects. In the absence of an effective vaccine, developing more specific antiviral therapies is urgently needed (24, 25). HCV, a positive-strand RNA virus with a genome size of 9.6 kb, has six major genotypes and numerous subtypes (26). The 5' nontranslated region (5' NTR) in the HCV genome is highly conserved among the six major genotypes, and this region contains an important structure known as the internal ribosome entry site that controls the initiation of HCV-RNA translation (27). Therefore, we chose this RNA genomic region as the target of nanozyme and synthesized alkylthiol-terminated DNA oligonucleotides containing an 18 nucleotide (nt)-long fragment with sequence complementary to that of the region (nt 322-339) in the HCV genome (FIG. 2.1). SiRNA 331—one of the most effective synthetic siRNAs against HCV replication—also targets this genome location (27), whereas its effective binding sequence is one nucleotide longer than the DNA oligonucleotides of the nanozyme (FIG. 2.1).

Anti-HCV nanozymes were prepared using a two-step method in which RNase-free water and buffer solutions were used (28). In a typical synthesis, gold nanocrystals (10 nM, 12.5 nm in diameter with a relative standard deviation of 8%) were first modified with RNase A (0.5 µM) in a carbonate buffered solution (2 mL; carbonate, 10 mM; pH 9.6). Then, the resultant RNase-gold nanoparticle conjugates were further functionalized with the alkylthiol-terminated, anti-HCV oligonucleotides (3.2 µM, FIG. 2.1). Oligonucleotide loading was promoted by stepwise addition of a concentrated NaCl solution (28). The resulting nanozymes were purified using ultracentrifugation and redispersed in water. On average, each of these nanozymes has about 12 RNase molecules and 78 oligonucleotide strands (28). The number of RNase molecules on a single nanozyme is tunable by varying the RNase concentration in the step of making RNase-gold nanoparticle conjugates (28). Indeed, a lower RNase concentration resulted in fewer RNase molecules, whereas the nanozyme that bears fewer RNase molecules supports more oligonucleotide strands. For instance, there are about 90 oligonucleotide strands on the nanozyme containing 7 RNase molecules. In this study, the anti-HCV nanozyme with 12 RNase molecules was used in the following in vitro and in vivo experiments.

To assess the target specificity of the anti-HCV nanozyme, we performed an in vitro RNase activity assay by using gold nanoparticle-oligonucleotide conjugates (Au-DNA, FIG. 2.1) as a negative control, and particle-free RNase A as the positive control. The target substrate was an HCV RNA segment (nt 1-1149), generated by in vitro transcription, that contains the entire 5'NTR region of the HCV RNA genome of the HCV JFH-1 strain (28). The control substrate was a 1257-nt RNA segment of human alpha-1 antitrypsin (AAT) gene—without complementary sequences to the nanozyme-bearing oligonucleotides—which was generated by in vitro transcription from a DNA plasmid (28). The HCV (or AAT) RNA (0.12 µM) was incubated with the anti-HCV nanozyme or a control in a phosphate-buffered saline solution (PBS, 11 µL; NaCl, 0.138 M; KCl, 0.027 M; pH 7.4) at 37° C. for 15 minutes, and the corresponding products were analyzed by electrophoresis in a denaturing agarose gel. Electrophoresis analyses show that the anti-HCV nanozyme exhibits no measurable cleavage activity on the AAT RNA, but it cleaves the HCV RNA target into two major fragments with a size of about 300 nt and 800 nt, respectively, which corresponds to a cleavage site matching the position where the nanozyme binds to the HCV RNA target via DNA/RNA hybridization (FIG. 2.1). In contrast, Au-DNA conjugates display no cleavage activity against either the HCV or AAT RNA, whereas unbound RNase A degrades both RNA substrates into short fragments which appeared as broad smear bands (FIG. 2.2). These results demonstrate that the anti-HCV nanozyme exhibits remarkable target specificity, and displays a RISC-like function—cleaving its target RNAs in a sequence—and site-specific manner. We attribute this RISC-like function to the cooperative coupling of the RNase and DNA-oligonucleotide components of nanozyme (FIG. 2.1). On one hand, the access of non-complementary RNAs to the nanozyme-bearing RNase molecules is likely blocked by the densely packed oligonucleotides through steric hindrance and repulsive coulomb interactions. On the other hand, these DNA oligonucleotides can also bind to target RNAs via base pairing and bring them to the RNase molecules on the nanozyme, resulting in the endonucleolytic cleavage of these RNAs into two fragments at positions close to the binding site (FIG. 2.1, FIG. 2.2).

Given the potential for RNase degradation by proteinases in the cell or in vivo (29), we next examined the in vitro resistance of the anti-HCV nanozyme against proteinase K compared with particle-free RNase A. RNase activity tests show that unbound RNase A lost its activity almost completely after the incubation with proteinase K in a PBS buffer (pH 7.4) at 37° C. for 1 h. In contrast, nearly no measurable change was observed in the nanozyme activity after an identical proteinase K treatment. We attribute the resistance to proteinase degradation to the fact that the RNase molecules on the nanozyme were protected by the tightly packed oligonucleotides via steric hindrance effects (FIG. 2.1). The ability to resist proteinase degradation should enhance the stability of these nanozymes in the cell and in vivo.

Previous work by others has demonstrated that Au-DNA conjugates are effective antisense agents for the control of gene regulation in cultured cells (21). This finding motivated us to explore whether nanozymes could efficiently cut target RNAs via a catalytic RNase H-dependent antisense pathway (21). We used an RNase H activity assay to compare the efficiency of this possible RNase H-dependent pathway with that of the RNase A-dependent nanozyme function (FIG. 2.1 and FIG. 2.3). Surprisingly, electrophoresis analyses show that RNase H exhibited little if any cleavage activity against the hybridized complexes of the 1149-nt HCV RNA and the Au-DNA conjugates, even in the case of using a high concentration of Au-DNA conjugate (3.4 nM) in a 5-h reaction (FIG. 2.3A). We attribute this extremely low RNase H activity to its inaccessibility to the DNA/RNA heteroduplexes formed on gold nanoparticles due to steric hindrance effects that are induced by the densely packed oligonucleotides and bulky target RNAs (FIG. 2.3B). Indeed, RNase H can effectively cleave the heteroduplexes of particle-free (i.e., unbound) DNA oligonucleotides and the HCV RNA (FIG. 2.3A). Also, these results are in full agreement with the result that RNase H did not lead to measurable effects on the reaction between the HCV RNA and the anti-HCV nanozyme (FIG. 2.3A). Together, these results suggest that it is the RNase A-dependent nanozyme function—but not the RNase H-dependent antisense mechanism—that plays a predominant role in the cleavage of target RNAs even in physiological environments where RNase H is available (e.g., in the cell and in vivo). Moreover, the RNase H-cleaved HCV RNA fragments have nearly identical sizes to the respective nanozyme-cleaved fragments (FIG. 2.3A), further confirming the results that the anti-HCV nanozymes indeed cleaved their target RNAs at the position close to the site where these RNAs bind to the nanozyme (FIG. 2.1).

To examine the activity of the nanozyme against HCV replication, we used a HCV replicon cell culture system, a FL-Neo cell line, which is a stable human hepatoma Huh7-derived cell line that harbors autonomously replicating genomic length genotype 1b HCV replicons (30). We first evaluated the cellular uptake and cytotoxicity of the nanozyme. The results from an inductively coupled plasmon (ICP) atomic emission-based assay indicate that about 90% of the nanozymes were taken up by FL-Neo cells after 48-h incubation; and cell viability tests using a MTS assay show that the nanozyme displayed no measurable toxicity to FL-Neo cells (28). We then examined the intracellular activity of the nanozyme with respect to gene knockdown for suppressing the replication of HCV RNA. FL-Neo cells were treated once with the nanozyme (or a control) at varying concentrations, incubated at 37° C. for 72 h, and then harvested and processed for viral RNA assay using a quantitative real-time reverse-transcription polymerase chain reaction (qRT-PCR), with the endogenous glyceraldehyde-3-phosphate dehydrogenase (GAPDH) gene as an internal standard. No measurable reduction in HCV-RNA levels was observed in the treatments using Au-DNA conjugates with concentrations of 0.034 and 0.14 nM, while the treatment with 0.54 nM Au-DNA conjugates resulted in a weak and statistically insignificant decrease in HCV RNA levels (FIG. 2.4). The inability of these conjugates to cause significant antisense effects on HCV replication is likely due to their low concentrations in our experiments. In contrast, when treated respectively with the same nanozyme dosages, HCV replication in the cells dramatically decreased, and the inhibitory effect was in a dose-dependent manner (FIG. 2.4). Moreover, the anti-HCV nanozymes outperformed lipoplex (Lipofectamine™ 2000, Invitrogen)-delivered siRNA 331 under the conditions studied with respect to percent HCV-RNA reduction (FIG. 2.4).

To further assess the intracellular antiviral activity of the nanozyme, we examined whether the nanozyme-mediated HCV-RNA reduction is associated with suppression of viral protein synthesis. In a typical experiment, FL-Neo cells were treated with the anti-HCV nanozyme (0.067 nM) or a control on day 1, 3, and 5 and then harvested on day 7 (31). Then the harvested cells were respectively processed for viral RNA assay using qRT-PCR and for protein assays using Western blotting and immunofluorescence staining (28). The non-structured 5A (NS5A) protein of HCV—which plays key roles in both viral RNA replication and modulation of the physiology of the host cell—was used to evaluate HCV protein levels in FL-Neo cells. The results from qRT-PCR analyses show that the nanozyme treatment resulted in 65% decrease in HCV-RNA levels in FL-Neo cells, whereas the treatment using the same amount of Au-DNA conjugates did not induce measurable effects on HCV RNA replication (FIG. 2.5A). Western blot analyses show fairly consistent results at the protein level: barely any effect was observed in the FL-Neo cells treated with Au-DNA conjugates, whereas the FL-Neo cells displayed a significant decrease in NS5A protein level of about 75% upon the nanozyme treatment (FIG. 2.5B). NS5A protein reductions slightly exceeded the reduction levels obtained from HCV RNA, and this could be due to post-transcriptional mechanisms that have been observed previously (32). In addition, the results from these ensemble measurements are consistent with those from single-cell level observations on the basis of fluorescent immunohistochemical staining for NS5A protein (FIG. 2.5C). After the nanozyme treatment, more than 99% of FL-Neo cells displayed a significant decrease in the levels of NS5A protein expression when compared to the control treatments (FIG. 2.5C). Altogether, these results unambiguously demonstrate that the anti-HCV nanozyme is capable of inducing an HCV gene knockdown in both the RNA and protein levels.

To evaluate the in vivo antiviral activity of the anti-HCV nanozyme, we constructed a xenotransplantation mouse model via subcutaneous injection of HCV-JFH1 infected Huh7.5 cells into non-obese diabetic/severe combined immunodeficiency (NOD/SCID) mice (28); HCV JFH1 is a genotype 2a strain capable of establishing robust infections in NOD/SCID mice harboring Huh7.5 hepatoma xenograft tumors (25, 33). The HCV-infected mice were randomly divided into three groups, and one group of mice without treatment was used as blank controls. The other two groups of mice were injected on day 1, day 3, and day 5 in the tumors with either the anti-HCV nanozyme or Au-DNA conjugates (3.4 pmol for each mouse, ~1.8 mg/kg). Treatment ended on day 7, when the animals were sacrificed and processed for viral RNA assay using qRT-PCR (note that no sign of toxicity was observed in any treated animals with either nanozyme or Au-DNA conjugates). The treatments with Au-DNA conjugates resulted in a statistically insignificant therapeutic effect on HCV RNA expression when compared with the control mice, which is consistent with those results from the in vitro experiments (FIG. 2.6). In contrast, the nanozyme caused a potent therapeutic anti-HCV effect in the mouse model; the nanozyme-treated mice displayed an average 99.7% decrease in HCV RNA levels. Significantly, the in vivo HCV RNA reductions exceeded the reduction levels observed in the corresponding in vitro experiments (FIG. 2.6). We attribute the improved antiviral therapeutic efficacy of the nanozyme to the fluidity and complex enzymatic characteristics of in vivo environments, which are much more dynamic systems than cell cultures (34).

When taken together, the results presented herein demonstrate that nanozyme—which exhibits a remarkable cooperative, RISC-like, gene silencing function—is a nanoparticle-based synthetic analog of the active RISC and an effective intracellular gene regulation agent for the suppression of HCV replication in cultured cells and in animal models. Importantly, since the antiviral function of nanozyme is independent from cellular RNAi machineries, nanozyme-mediated RNA silencing does not in principle interfere with naturally occurring gene regulation pathways mediated by microRNAs and cannot be inhibited by the RNAi suppressors encoded by pathogenic human viruses (e.g., HCV, HIV). Therefore, this nanoparticle-based gene regulation approach complements RNAi-based approaches and has the potential to become a general experimental tool for functional genomics as well as a simple, straightforward and effective therapeutic tool for viral infections, cancers, and other diseases associated with protein expression. Moreover, this platform will allow one to add functionality that could direct nanozyme agents to specific tissues, organs, and even sub-cellular organelles that express target genes (17). Furthermore, nanozyme constitutes a step toward a new class of nanoparticle-based intercellular machineries with extraordinary cooperative functions, remarkable target selectivity, and perhaps allosteric functions that enable these machineries to have an on/off switch in response to chosen allosteric effectors such as specific byproducts in disease-associated metabolism pathways (35), thus providing a powerful tool for studying and regulating a wide variety of biological pathways such as those in somatic cell reprogramming.

References of Example 2, Each of Which are Incorporated Herein by Reference
1. A. Z. Fire, Gene silencing by double-stranded RNA (Nobel Lecture). *Angew. Chem. Int. Ed.* 46, 6967 (2007).
2. C. C. Mello, Return to the RNAi world: rethinking gene expression and evolution (Nobel Lecture). *Angew. Chem. Int. Ed.* 46, 6985 (2007).
3. B. Alberts, *Molecular biology of the cell.* (Garland Science, New York, ed. 5th, 2008).
4. D. Castanotto, J. J. Rossi, The promises and pitfalls of RNA-interference-based therapeutics. *Nature* 457, 426 (2009).
5. M. E. Davis et al., Evidence of RNAi in humans from systemically administered siRNA via targeted nanoparticles. *Nature* 464, 1067 (2010).
6. D. Bumcrot, M. Manoharan, V. Koteliansky, D. W. Y. Sah, RNAi therapeutics: a potential new class of pharmaceutical drugs. *Nat. Chem. Biol.* 2, 711 (2006).
7. D. Grimm et al., Fatality in mice due to oversaturation of cellular microRNA/short hairpin RNA pathways. *Nature* 441, 537 (2006).
8. J. Kurreck, RNA interference: from basic research to therapeutic applications. *Angew. Chem. Int. Ed.* 48, 1378 (2009).
9. J. Ji et al., Suppression of short interfering RNA-mediated gene silencing by the structural proteins of hepatitis C virus. *J. Gen. Virol.* 89, 2761 (2008).
10. R. Triboulet et al., Suppression of microRNA-silencing pathway by HIV-1 during virus replication. *Science* 315, 1579 (2007).
11. W. C. W. Chan, S. M. Nie, Quantum dot bioconjugates for ultrasensitive nonisotopic detection. *Science* 281, 2016 (1998).
12. P. Alivisatos, The use of nanocrystals in biological detection. *Nat. Biotechnol.* 22, 47 (2004).
13. W. Wu, A. D. Li, Optically switchable nanoparticles for biological imaging. *Nanomedicine (Lond)* 2, 523 (2007).
14. H. M. Song, Q. S. Wei, Q. K. Ong, A. Wei, Plasmon-resonant nanoparticles and nanostars with magnetic cores: synthesis and magnetomotive imaging. *ACS Nano* 4, 5163 (2010).
15. D. Graham, K. Faulds, Surface-enhanced Raman scattering as a detection technique for molecular diagnostics. *Expert. Rev. Mol. Diagn.* 9, 537 (2009).

16.1. Brigger, C. Dubernet, P. Couvreur, Nanoparticles in cancer therapy and diagnosis. *Adv. Drug. Delivery Rev.* 54, 631 (2002).
17. D. Peer et al., Nanocarriers as an emerging platform for cancer therapy. *Nat. Nanotechnol.* 2, 751 (2007).
18. B. Duncan, C. Kim, V. M. Rotello, Gold nanoparticle platforms as drug and biomacromolecule delivery systems. *J. Control Release* 148, 122 (2010).
19. M. V. Yezhelyev, L. F. Qi, R. M. O'Regan, S, Nie, X. H. Gao, Proton-sponge coated quantum dots for siRNA delivery and intracellular imaging. *J. Am. Chem. Soc.* 130, 9006 (2008).
20. C. A. Mirkin, R. L. Letsinger, R. C. Mucic, J. J. Storhoff, A DNA-based method for rationally assembling nanoparticles into macroscopic materials. *Nature* 382, 607 (1996).
21. N. L. Rosi et al., Oligonucleotide-modified gold nanoparticles for intracellular gene regulation. *Science* 312, 1027 (2006).
22. S. J. Park, T. A. Taton, C. A. Mirkin, Array-based electrical detection of DNA with nanoparticle probes. *Science* 295, 1503 (2002).
23. W. L. Tsai, R. T. Chung, Viral hepatocarcinogenesis. *Oncogene* 29, 2309 (2010).
24. R. E. Lanford et al., Therapeutic silencing of microRNA-122 in primates with chronic hepatitis C virus infection. *Science* 327, 198 (2010).
25. A. Ploss, C. M. Rice, Towards a small animal model for hepatitis C. *EMBO Rep.* 10, 1220 (2009).
26. L. K. McMullan et al., Evidence for a functional RNA element in the hepatitis C virus core gene. *Proc. Natl. Acad. Sci. U.S.A.* 104, 2879 (2007).
27. T. Yokota et al., Inhibition of intracellular hepatitis C virus replication by synthetic and vector-derived small interfering RNAs. *EMBO Rep.* 4, 602 (2003).
28. See supporting material below.
29. B. M. Kelly, C. Z. Yu, P. L. Chang, Presence of a lysosomal-enzyme, arylsulfatase-a, in the prelysosome-endosome compartments of human cultured fibroblasts. *Eur. J. Cell Biol.* 48, 71 (1989).
30. G. Randall, A. Grakoui, C. M. Rice, Clearance of replicating hepatitis C virus replicon RNAs in cell culture by small interfering RNAs. *Proc. Natl. Acad. Sci. U.S.A.* 100, 235 (2003).
31. Please note that no measurable changes in the total RNA amount of FL-Neo cells were observed in the treatment with either the nanozyme or Au-DNA conjugates, indicating that these treatments did not interfere with cell proliferation.
32. T. Kanda, R. Steele, R. Ray, R. B. Ray, Small interfering RNA targeted to hepatitis C virus 5' nontranslated region exerts potent antiviral effect. *J. Virol.* 81, 669 (2007).
33. C. Guevin, A. Lamarre, P. Labonte, Novel HCV replication mouse model using human hepatocellular carcinoma xenografts. *Antiviral Res.* 84, 14 (2009).
34. B. D. Lindenbach, C. M. Rice, Unravelling hepatitis C virus replication from genome to function. *Nature* 436, 933 (2005).
35. J. P. Changeux, S. J. Edelstein, Allosteric mechanisms of signal transduction. *Science* 308, 1424 (2005).

Supplemental Information for Example 2
Materials and Methods

Materials: Thiol-modified anti-HCV DNA oligonucleotides were purchased from Bio-synthesis Inc. RNase-free water and siRNA 331 were purchased from Thermo Scientific, USA. RNase A (ribonuclease A from bovine pancreas), and RNase H (ribonuclease H from *Escherichia coli*), RNase-free buffers, and chemicals were ordered from Sigma-Aldrich.

Nanoparticle Synthesis. Citrate-stabilized gold nanoparticles (12.5 nm in diameter with a relative standard deviation of 8%, FIG. 1.3.) were prepared according to literature procedures (S1).

Synthesis of Nanoparticle-based RNA Silencing Complex (nanozyme). Gold nanoparticles (10 nM, 12.5 nm in diameter with a relative standard deviation of 8%) were mixed with RNase A (0.5 μM) in a carbonate buffered solution (2 mL; carbonate, 10 mM; pH 9.6) (S2, S3). Under shaking for 30 min, alkylthiol-modified anti-HCV oligonucleotides (6.4 nmol) and phosphate buffer (1.0 M, pH 7.4) were added to bring the mixture solution with 10 mM phosphate. After 8 h shaking, sodium chloride (2.0 M solution in RNase-free water) was added to bring the NaCl concentration gradually to 0.3 M during a period of 32 h. The solution was further shaken for another 8 h. Then the resulting nanozyme particles were centrifuged (13000 rpm, 20 min, for three times) and redispersed in RNase-free water. In addition, the number of RNase A loaded onto individual nanozymes can be controlled by varying the concentration of RNase A. Note that all the vials and tubes used herein were modified by silane for minimizing the nonspecific binding of RNase A onto the glass surface of these glass containers.

RNase A Loading Determination: The average number of RNase A molecules loaded onto a single nanozyme was determined by a subtraction method. The total amount of RNase molecules loaded on to gold nanoparticles in a synthesis batch was determined by subtracting the amount of unloaded RNase molecules from the amount of RNase molecules added initially. This total loading amount was then divided by the total number of nanozymes in the solution, yielding the average number of RNase A per single nanozyme. The number of nanozymes was determined by using UV-Vis absorption spectroscopy ($\lambda$=524 nm, $\varepsilon$=2.0×$10^8$ $M^{-1}$ $cm^{-1}$). The amount of unloaded RNase in a reaction solution was determined by measuring the RNase activity of the supernatant resulted after removal of nanozymes (FIG. 2.7). A typical RNase activity measurement was performed according to the literature method, in which cytidine-2',3'-phosphate was used as the substrate (S4). Then the amount of RNase molecules was obtained using a standard RNase activity curve (Initial reaction rate as a function of RNase concentration: 0, 0.1, 0.2, 0.4, 0.6, 0.8, 1.0, 2.0, 3.0, 4.0 μg/mL were chosen, FIG. 2.7). Note that all the vials and tubes used in this experiment were modified by silane for minimizing the nonspecific binding of RNase A onto the surface of these glass containers.

DNA Loading Determination: The number of nanozymes or gold nanoparticle-DNA conjugates (Au-DNA) were determined by using UV-Vis spectroscopy ($\lambda$=524 nm, $\varepsilon$=2.0×$10^8$ $M^{-1}$ $cm^{-1}$). DNA oligonucleotides were released from nanozymes or Au-DNA conjugates by dissolving their gold nanoparticle backbones in 0.1 M KCN solution. The number of DNA molecules per nanoparticle was determined using oligonucleotide quantification kit (Oligreen; Invitrogen) following the manufacturers' recommendations. DNA loading number was calculated by dividing the concentration of oligonucleotides by the concentration of gold nanoparticles (S5).

Synthesis of RNA Substrates Using in vitro Transcription. The pJFH1 plasmid was a gift from Dr Takaji Wakita (National Institute of Infectious Diseases, Tokyo, Japan) (S6). The human AAT gene was amplified from a patient liver tissue and cloned into pEF6/V5-His-TOPO vector (Invitrogen). The expression vector pTOPO-AAT was sequenced using the Big Dye Terminator V3.1 Kit from Applied Biosystems (Foster City, Calif.). The pJFH1 was cut by using Cla I, and the pTOPO-AAT was cut by Xba I. The resulting linearized DNA plasmids were purified and used as the templates for in vitro transcription to make the HCV RNA segment (nt 1-1149) or the 1257-nt AAT RNA using MEGAscript T7 kit (Ambion, Austin, Tex.).

RNase A Activity Assay. In a typical test, RNA substrates (0.5 μg) were incubated with nanozyme (0.034 nM), or Au-DNA conjugates (0.034 nM), or particle-free RNase A (0.408 nM) in a phosphate buffered saline solution (11 μL; phosphate, 10 mM; NaCl, 0.138 M; and KCl, 0.027 M) for 15 min. Then the formaldehyde loading buffer (11 μL, purchased from Londa Rockland, Inc.) was added to denature the RNA products, and the resulting solution was heated at 65° C. for 11 min, and then immediately placed on ice for 2 min before loading onto a 2% agarose/formaldehyde denaturing gel (10×MOPS buffer, 5 mL: RNase free water, 45 mL; agarose, molecular biology grade, 1.0 g; and 37% formaldehyde solution, 0.9 mL). Gel electrophoresis was performed at 60 V for approximately 90 min or until the front line of bromophenol blue dyes migrated about 6 cm in the gel. Afterwards, the gel was stained by SYBR Green II for visualization.

Proteinase K Resistance Tests. In a typical proteinase K resistance test, nanozymes (0.034 nM) or particle-free RNase A (0.408 nM) was first incubated with proteinase K (10 nM) in a PBS buffer (pH 7.4) at 37° C. for 1 h. Then the product of this proteinase K treatment was divided into two parts and further incubated with the HCV (or AAT) RNA (0.12 μM) in a PBS buffer (11 μL; pH 7.4) at 37° C. for 15 minutes. The products were analyzed by using electrophoresis in a 2% formaldehyde agarose gel as described above.

RNase H Activity Assay. In a typical test, RNase H (1 unit) was incubated with HCV RNA segment (nt 1-1149, 0.12 μM) and nanozyme (0.034 nM), or Au-DNA 1 with the conjugate concentration of 0.034 M, or Au-DNA 2 and 3, with the conjugate concentration of 3.4 nM in a Tris-HCl buffer (11 μL; pH 8.0; KCl, 50 mM; $MgCl_2$, 4 mM; and DTT, 1 mM) at 37° C. The reaction time was 15 min except when a 5-h reaction was performed in the test with Au-DNA 3. In addition, a reaction with only the HCV RNA and the nanozyme was carried out as a control to compare the reaction with RNase H. The resulting products were analyzed by using electrophoresis in a 2% formaldehyde agarose gel as described above.

Cell Culture and Antiviral Activity of nanozyme as Compared with That of siRNA 331. FL-Neo cells were grown in Dulbecco's modified Eagle medium, supplemented with 10% fetal bovine serum, 200 μmol/L L-glutamine, 10 mM nonessential amino acids, and antibiotics at 37° C. in 5% $CO_2$. To evaluate the antiviral activity of nanozyme, FL-Neo cells were seeded onto 12-well plates and cultured overnight. The FL-Neo cells were incubated with the anti-HCV nanozyme, and Au-DNA conjugates, or transfected with siRNA 331 at three different doses (0.034, 0.14, and 0.54 nM) (FIG. 2.4). The siRNA 331 designed to target the 5' nontranslated region (5' NTR) of the HCV genome (S7) was synthesized from Thermo Scientific (USA). Transfection of the siRNA oligonucleotides were performed by using Lipofectamine™ 2000 reagent (Invitrogen) in accordance with the manufacture's instructions. In addition, the experiments with a blank control and a control with Lipofectamine™ 2000 were also performed. After 72-h incubation, the FL-Neo cells were harvested and processed for quantitative reverse transcribed real-time PCR analyses (qRT-PCR, see below for details on the analyses).

Cell Proliferation Assay. FL-Neo cells were dispensed into 96-well plates at a final concentration of $3 \times 10^3$ cells/well in a culture medium (100 μL), and incubated overnight before treatment. The culture media was then removed and replaced with new medium with the anti-HCV nanozyme of varying concentrations (0.034, 0.068, 0.14, 0.27, 0.54 nM) (FIG. 2.8). After 72 h treatment, cell viability was measured using the MTS (3-(4,5-dimethylthiazol-2-yl)-5-(3-carboxymethoxy-phenyl)-2-(4-sulfophenyl)-2H-tetrazolium) cell proliferation assay (Promega). The cells were incubated for 3 h after addition of MTS/PMS (phenazine methosulfate) solution to allow for color development, and then the absorbance values were read at 492 nm using a Multiscan plate reader.

Antiviral Effects of nanozyme in FL-Neo Cells on both the HCV RNA and Viral Protein Expressions. FL-Neo cells were seeded onto 35-mm wells of a six-well cell culture plate and cultured overnight. The FL-Neo cells were treated on day 1, day 3 and day 5 with fresh media containing 0.068 nM nanozymes (or Au-DNA conjugates). Control cells were incubated only with the culture medium. Treatment ended on day 7 when the cells were harvested, divided into three parts and then processed for qRT-PCR analyses, Western blot analyses and single-cell level immunofluorescence imaging (see below for technique details on these analyses).

Antiviral Effects of nanozyme in a HCV-infected Xeno-transplantation Mouse Model. Xenographed mice harboring HCV were constructed as follows. First, HCV transfected human cells (Huh7.5 cells) were generated. The pJFH1 plasmid was cut by Xba I, and the resulting linearized DNA was purified and used as the template for in vitro transcription. In vitro transcribed JFH1 RNA was delivered into Huh7.5 cells by electroporation. HCV replication in transfected cells was confirmed by NS5A immunostaining. The tumorigenicity of Huh7.5 HCV transfected cells was performed by inoculating $5 \times 10^6$ cells, resuspended in PBS (100 μl, pH 7.4), subcutaneously into the non-obese diabetic/severe combined immunodeficiency (NOD/SCID) mice (8 to 10-week). The tumor volume of mice was evaluated twice a week. When tumors reached 300-500 $mm^3$, mice (each mouse ~22 g) were randomly divided into three groups. One group was set up as controls without any treatment. Another two groups were injected on day 1, day 3 and day 5 with nanozyme or Au-DNA conjugates (sterile PBS, 100 μl; 3.4 pmol, ~1.8 mg/kg). Treatment ended on the 7th day when the mice were sacrificed and processed for HCV RNA assay using qRT-PCR. In these experiments, mice were bred and maintained in microisolators under pathogen-free conditions. All experimental procedures were performed in accordance with the recommendations in the Guide for the Care and Use of Laboratory Animals of the National Institutes of Health. The protocol was approved by the committee on the Animal Care Service of the University of Florida (Permit Number: 200801081).

RNA Extraction and qRT-PCR. RNA samples were extracted from FL-Neo cells or mouse tumor tissues using an RNA isolation reagent (TRIzol; Invitrogen, Carlsbad, Calif.). To prevent DNA contamination, total RNA was treated with RNase-free DNase II (Invitrogen). Total RNA samples (2 μg per reaction) were reversely transcribed into cDNAs by RT II reverse transcriptase (Invitrogen). Then, the cDNAs were used as templates in quantitative real-time PCR with HCV 3'NTR gene-specific primers (i.e., FP 5'-CCTTCTTTAATGGTGGCTCCAT-3' (SEQ ID No: 1): nt 9538-9559; RP 5'-GGCTCACGGACCTTTCACA-3' SEQ ID No: 2: nt 9582-9600, Probe 5'-TTAGCCCTAGTCACG-GCT-3' SEQ ID No: 3: nt 9561-9578). The amplification reactions were performed TaqMan RT-PCR on a StepOne Plus real-time PCR system (Applied Biosystems, Foster City, Calif.). The human glyceraldehyde-3-phosphate dehydrogenase gene (GAPDH; FP 5'-TCACCAGGGCT-GCTTTTA-3' SEQ ID No: 4; and RP 5'-TTCACACCCAT-GACGAACA-3' SEQ ID No: 5) was used as an internal control in PCR amplification.

Western Blot Analysis. Cell lysates were prepared by treating samples with ice-cold lysis Tris-HCl buffer (20 mM, pH 7.8; NP40, 10%; glycerol, 10%; NaCl, 137 mM; EDTA, 10 mM), and protease inhibitor cocktail (Roche Applied Science, Mannheim, Germany) for 20 min on ice followed by centrifugation at 4° C. for 15 min to sediment particulate materials. Proteins then were separated by SDS-PAGE (10% acrylamide), transferred to nitrocellulose membranes, and then blocked with 5% skim milk in a phosphate-buffered saline. Mouse-anti-HCV NS5A antibody was used as the primary antibody (1:250) and peroxidase-conjugated goat anti-mouse IgG antibody (Sigma-Aldrich) was used as the secondary antibody (1:1000). Beta-actin was detected by an antibody (1:8000, clone AC-74, Sigma-Aldrich) and used as a loading control. Signals were detected by using the Supersignal® west Pico chemiluminescent substrate (PIERCE) according to the manufacturer's directions (S8).

Immunofluorescence Imaging. FL-Neo cells were transferred onto glass cover slips and fixed with 5% acetic acid in ethanol. The cells were washed with phosphate-buffered saline and incubated with monoclonal antibody to HCV NS5A protein for 1 hour. The secondary antibody was FITC-labeled goat anti-mouse immunoglobulin G antibody. The nuclei were counterstained with 4',6-diamidino-2-phenylindole (DAPI; Vector Laboratories Inc, Burlingame, Calif.), followed by examination under a fluorescence microscope (Nikon TE-2000 microscope, Nikon, Melville, N.Y.) (S9).

References for the Supporting section of Example 2, each of which is incorporated by reference:

S1. K. C. Grabar, R. G. Freeman, M. B. Hommer, M. J. Natan, Preparation and characterization of Au colloid monolayers. *Anal. Chem.* 67, 735-743 (1995).

S2. M. Bendayan, Ultrastructural localization of nucleic acid by the use of enzyme-gold complexes. *J. Histochem. Cytochem.* 29, 531 (1981).

S3. M. Bendayan, The enzyme-gold cytochemical approach: a review, chap. 8 in M. A. Hayat, *Colloid gold: principles, methods, and applications*. (Academic Press, San Diego, 1989) vol. 2.

S4. E. M. Crook, A. P. Mathias, B. R. Rabin, Spectrophotometric assay of bovine pancreatic ribonuclease by the use of cytidine 2':3'-phosphate. *Biochem. J.* 74, 234 (1960).

S5. A. E. Prigodich, O.-S. Lee, W. L. Daniel, D. S. Seferos, G. C. Schatz, C. A. Mirkin, Tailoring DNA structure to increase target hybridization kinetics on surfaces. *J. Am. Chem. Soc.* 132, 10638 (2011).

S6. T. Wakita, T. Pietschmann, T. Kato, T. Date, M. Miyamoto, Z. Zhao, K. Murthy, A. Habermann, H.-G. Krausslich, M. Mizokami, R. Bartenschlager, T. J. Liang, Production of infectious hepatitis C virus in tissue culture from a cloned viral genome. *Nature Med.* 11, 791 (2005)

S7. T. Yokota, N. Sakamoto, N. Enomoto, Y. Tanabe, M. Miyagishi, S. Maekawa, L. Yi, M. Kurosaki, K. Taira, M. Watanabe, H. Mizusawa, Inhibition of intracellular hepatitis C virus replication by synthetic and vector-derived small interfering RNAs. *EMBO Rep.* 4, 602 (2003).

S8. F. Sambrook, E. F. Fritsch, T. Maniatis, *Molecular cloning: a laboratory manual* (Cold Spring Harbor Laboratory Press, New York, Ed. 2, 1989) pp. 1860-1865.

S9. H. Z. Zhu, H. J. Dong, E. Eksioglu, A. Hemming, M. Cao, J. M. Crawford, D. R. Nelson, C. Liu, Hepatitis C virus triggers apoptosis of a newly developed hepatoma cell line through antiviral defense system. *Gastroenterology* 133, 1649-1659 (2007).

Example 3

Materials: Thiol-modified thrombin 15mer-aptamers (GGT-TGG-TGT-GGT-TGG T20) were purchased from Bio-synthesis Inc. Human α-Thrombin and human plasmin were ordered from Heamatologic Technologies Inc., and RNase A (ribonuclease A from bovine pancreas), Proteinase K (from *tritirachium album*), chromogenic substrates and chemicals were ordered from Sigma-Aldrich. Thiol-modified PEG (Poly Ethylene Glycol) was ordered from Laysan Bio Inc.

Synthesis of thrombin-selective nanozyme (FIG. 3.1). Gold nanoparticles (5 nM, 12.5 nm in diameter with a relative standard deviation of 8%) were mixed with Proteinase K (0.2 µM) in a carbonate buffered solution (2 mL; carbonate, 10 mM; pH 9.6). Under shaking for 30 min, 1.0 mM $CaCl_2$ was added then incubated for overnight at 4° C. Alkylthiol-modified thrombin 15mer-aptamer (1.0 µM: GGT-TGG-TGT-GGT-TGG) and phosphate buffer (1.0 M, pH 7.4; Tween 20, 0.01%) were added to bring the mixture solution with 10 mM phosphate. After 20 min shaking, the solutions were sonicated for 10 sec, and then sodium chloride (2.0 M solution) was added to bring the NaCl concentration gradually to 0.3 M every 20 min with 10 sec sonication. Lastly, thiol-modified PEG (8.0 µM) was added. The solution was further shaken for overnight at 4° C. Then the resulting NZ particles were centrifuged (15000 rpm, 20 min, for four times) and re-dispersed in phosphate buffer (10 mM; NaCl, 0.154 M; KCl, 0.005 M; $CaCl_2$, 0.001 M; $MgCl_2$, 0.005 M; Glycerol, 5%; and Tween 20, 0.01%).

Nanozyme selectivity assay (FIG. 3.2). In a typical test, thrombin substrates (0.05 µM) were incubated with 0.5 nM of thrombin-selective nanozyme (or a control nanozyeme that was functionalized with oligonucleotides: GGT-TGG-TGT-GGT-AAA SEQ ID No: 6 (15mers-s), or TTT-TTT-TTT-TTT-TTT, SEQ ID No: 7) in a phosphate buffered saline solution (1 mL; phosphate, 10 mM; NaCl, 0.154 M; KCl, 0.005 M; $CaCl_2$, 0.001 M; $MgCl_2$, 0.001 M; Glycerol, 5%; and Tween 20, 0.01%) for 0 (10 min), 3, 6, 9 and 12 hr at 37° C. Then the solutions were centrifuged to remove the particles (15000 rpm, 30 min) and the remaining amount of thrombin in a supernatant was measured through UV-Vis absorption spectroscopy at 405 nm (thrombin substrate, β-Ala-Gly-Arg-p-nitroanilide, 0.5 mM).

Selectivity Assay (FIG. 3.3). For selectivity test, thrombin (0.05 µM), plasmin (0.05 µM) and RNase A (0.2 µM) were incubated with NZ (0.5 nM) in a phosphate buffered saline solution (1 mL; phosphate, 10 mM; NaCl, 0.154 M; KCl, 0.005 M; $CaCl_2$, 0.001 M; $MgCl_2$, 0.005 M; Glycerol, 5%; and Tween 20, 0.01%) for 0 (10 min), 2, 4, 6 and 8 hr at 37° C. Then the solutions were centrifuged to remove the particles (15000 rpm, 30 min) and the remaining amount of thrombin, plasmin and RNase A in a supernatant was measured through UV-Vis absorption spectroscopy (thrombin substrate, β-Ala-Gly-Arg-p-nitroanilide, 0.5 mM at 405 nm; plasmin substrate, H-D-Val-Leu-Lys-p-nitroanilide, 0.05 mM at 405 nm; RNase A substrate, cytidine-2',3'-phosphate, 0.1 mg/mL at 286 nm).

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A nanozyme, comprising:
   a nanoparticle having an enzyme and a plurality of recognition moieties attached thereto, and optionally having one or more protecting moieties attached thereto,
   wherein the recognition moieties target a specific target molecule that reacts with the enzyme, and
   wherein the recognition moieties and protecting moieties are at a density on the nanoparticle that substantially reduces non-target molecules from reacting with the enzyme.

2. The nanozyme of claim 1, wherein the enzyme does not react with the recognition moieties and the protecting moieties.

3. The nanozyme of claim 1, where at least two different types of enzymes are attached to the nanoparticle.

4. The nanozyme of claim 1, wherein the enzyme is selected from the group consisting of: an endoribonucleases, an endodeoxyribonuclease, an endoproteinase, and a combination thereof.

5. The nanozyme of claim 1, wherein the enzyme has a function selected from the group consisting of: hydrolysis, methylation, de-methylation, phosphorylation, oxidation, reduction, nucleic acid editing, and condensation.

6. The nanozyme of claim 1, wherein the nanoparticle is selected from the group consisting of: a quantum dot, a metal nanoparticle, a magnetic nanoparticle, a metal oxide nanoparticle, a heterogeneous dimer, trimer, oligomer, and polymer nanoparticle, an assembly of multiple nanoparticles, a composite organic/inorganic nanoparticle, a single walled nanotube, a multiwalled nanotube, and graphene.

7. The nanozyme of claim 1, wherein at least one of the recognition moieties is selected from the group consisting of: a sequence-specific DNA oligonucleotide, a locked nucleic acid (LNA), a peptide nucleic acid (PNA), an antibody, and a small molecule protein receptor.

8. The nanozyme of claim 1, wherein the target molecule is selected from the group consisting of: a DNA, a RNA, and a protein.

9. The nanozyme of claim 1, further comprising at least one protecting moiety, wherein the protecting moiety is attached to the nanoparticle.

10. The nanozyme of claim 9, wherein the protecting moiety is chosen from the group consisting of: a DNA oligonucleotide, a locked nucleic acid (LNA), a peptide nucleic acid (PNA), a poly(ethylene glycol) (PEG), a poly (vinyl alcohol) (PVA), a poly(acrylic acid) (PAA), a poly (propylene furmarate-co-ethylenee glycol) (P(PF-co-EG)), a polyacrylamide, a polypeptide, a poly-N-substituted glycine oligomer (polypeptoid), a hyaluronic acid (HA), an alginate, a chitosan, an agarose, a collagen, a fibrin, a gelatin, a dextran, derivatives of each of these ligands, and a combination thereof.

11. The nanozyme of claim 10, wherein the enzyme is selected from the group consisting of: an endoribonucleases, an endodeoxyribonuclease, an endoproteinase, and a combination thereof;

wherein the nanoparticle is selected from the group consisting of: a quantum dot, a metal nanoparticle, a magnetic nanoparticle, a metal oxide nanoparticle, a heterogeneous dimer, trimer, oligomer, and polymer nanoparticle, a composite organic/inorganic nanoparticle, a single walled nanotube, a multiwalled nanotube, and graphene;

and wherein the recognition moiety is selected from the group consisting of: a sequence-specific DNA oligonucleotide, a locked nucleic acid (LNA), a peptide nucleic acid (PNA), an antibody, and a small molecule protein receptor.

12. The nanozyme of claim 9, wherein the protecting moiety has a function selected from the group consisting of: cell-uptake efficiency, selective cell-entry efficiency, substantially no toxicity, substantially no immunogenicity, and a combination thereof.

13. The nanozyme of claim 1, further comprising a therapeutic agent.

14. The nanozyme of claim 1, wherein the nanoparticle functions as an imaging agent.

15. The nanozyme of claim 1, further comprising an inter-and intra-cellular traffic guiding moiety attached to the nanoparticle.

16. The nanozyme of claim 1, further comprising an allosterically functional moiety, attached to the nanoparticle.

17. The nanozyme of claim 1, further comprising the protecting moieties, wherein the protecting moieties provide an additional function selected from the group consisting of increasing colloidal stability of the nanozyme, substantially reducing the toxicity of the nanozyme, substantially reducing the immunogenicity of the nanozyme, and a combination thereof.

* * * * *